US012559782B2

(12) United States Patent
Bodie et al.

(10) Patent No.: US 12,559,782 B2
(45) Date of Patent: Feb. 24, 2026

(54) FUNGAL STRAINS COMPRISING ENHANCED PROTEIN PRODUCTIVITY PHENOTYPES AND METHODS THEREOF

(71) Applicant: DANISCO US INC., Palo Alto, CA (US)

(72) Inventors: Elizabeth A. Bodie, Belmont, CA (US); Zhongqiang Chen, Wilmington, DE (US); Chuanbin Liu, Menlo Park, CA (US); Michael Ward, San Francisco, CA (US)

(73) Assignee: DANISCO US INC., Palo Alto, CA (US)

( * ) Notice: Subject to any disclaimer, the term of this patent is extended or adjusted under 35 U.S.C. 154(b) by 955 days.

(21) Appl. No.: 17/766,902

(22) PCT Filed: Nov. 6, 2020

(86) PCT No.: PCT/US2020/059379
§ 371 (c)(1),
(2) Date: Apr. 6, 2022

(87) PCT Pub. No.: WO2021/092356
PCT Pub. Date: May 14, 2021

(65) Prior Publication Data

US 2024/0102070 A1 Mar. 28, 2024

Related U.S. Application Data

(60) Provisional application No. 62/932,525, filed on Nov. 8, 2019.

(51) Int. Cl.

| | |
|---|---|
| ***C12P 1/02*** | (2006.01) |
| ***C07K 14/00*** | (2006.01) |
| ***C12N 9/22*** | (2006.01) |
| ***C12N 9/24*** | (2006.01) |
| ***C12N 15/11*** | (2006.01) |
| ***C12N 15/52*** | (2006.01) |
| ***C12N 15/80*** | (2006.01) |
| ***C12N 15/90*** | (2006.01) |
| ***C12P 21/00*** | (2006.01) |
| ***C12P 21/02*** | (2006.01) |

(52) U.S. Cl.
CPC ................ *C12P 21/02* (2013.01); *C12N 9/22* (2013.01); *C12N 9/2402* (2013.01); *C12N 15/11* (2013.01); *C12N 15/905* (2013.01); *C12Y 302/01* (2013.01); *C12N 2310/20* (2017.05); *C12N 2800/80* (2013.01)

(58) Field of Classification Search
CPC .............. C12N 9/2437; C12N 2310/20; C12N 2800/80; C12N 2800/245; C12P 21/02; C12P 7/06; C12Y 302/01091
See application file for complete search history.

(56) References Cited

U.S. PATENT DOCUMENTS

| | | | | |
|---|---|---|---|---|
| 10,745,679 B2 * | 8/2020 | Persillon | .................. | C12P 7/10 |
| 2008/0233175 A1 * | 9/2008 | Steer | ...................... | A23L 33/18 424/439 |
| 2017/0152497 A1 * | 6/2017 | Persillon | ............. | C12N 9/2437 |

FOREIGN PATENT DOCUMENTS

| | | |
|---|---|---|
| WO | 2016130523 A1 | 8/2016 |

OTHER PUBLICATIONS

Metz et al., J.B.C., 281(1), 410-417, 2006.*
International Search Report from PCT Application No. PCT/US2020/059379 dated Apr. 8, 2021, 5 pages.
Written Opinion from PCT Application No. PCT/US2020/059379 dated Apr. 8, 2021, 5 pages.
International Preliminary Report on Patentability from PCT Application No. PCT/US2020/059379 dated May 10, 2022, 6 pages.
Flis et al., "The Gef1 protein of *Saccharomyces cerevisiae* is associated with chloride channel activity", Biochemical and Biophysical Research Communications, vol. 294, Issue 5, pp. 1144-1150, 2002.
Iwaki et al., "Role of guanine nucleotide exchange factors for Rho family GTPases in the regulation of cell morphology and actin cytoskeleton in fission yeast", Biochem Biophys Res Commun; 312(2):414-420, 2003.
Metz et al. "The Yeast Arr4p ATPase Binds the Chloride Transporter Gef1p When Copper Is Available in the Cytosol", The Journal of Biological Chemistry vol. 281, No. 1, pp. 410-417, Jan. 6, 2006.
Oddon et al., "A CLC chloride channel plays an essential role in copper homeostasis in Aspergillus nidulans at increased extracellular copper concentrations", Biochimica et Biophysica Acta 1768, 2466-2477, 2007.

* cited by examiner

*Primary Examiner* — Maryam Monshipouri

(57) ABSTRACT

The present disclosure is generally related to modified filamentous fungal strains (cells) comprising enhanced protein productivity phenotypes, wherein such modified strains are particularly well-suited for growth in submerged cultures (e.g., large-scale production of proteins for industrial/commercial applications). Thus, certain embodiments of the disclosure are related to such variant (modified) strains of filamentous fungus derived (obtained) from parental strains comprising a gene encoding a native GEF1 protein, wherein the variant strain comprises a genetic modification which disrupts or deletes a gene encoding a native GEF1 protein, wherein the variant strain comprises an increased protein productivity phenotype (i.e., relative to the parental strain) when grown/cultivated/fermented under the same conditions.

15 Claims, 6 Drawing Sheets

Specification includes a Sequence Listing.

(SEQ ID NO: 1)
ATGGACCCGGACCCGGACCTGCACCTGCCAGCACGAGTAGAGCGCGCGAGCCTGGATGGTAGCGTGTTTG
TAGCCCACGATGCGCATCCGCCGGCTCGCCATCTGCCCCATCTCCATCTCCCCCAGCTGGCCCATCCAGC
CTCAAACTCAACCTCCAACTTCACCTTGCGCTCGCACTCGCACTCGCCCGCTGCCGGCGACGTCGTCCTG
CCCGCCTCAACCGCCAATGCCCACGTCCTCGCCCACCATGCAGCTGCCACCCTAGATCCTGACGACTACT
ACAGGAGCTACGAGACAGCCTCCAGCCCCGGCGGCGAGCCACAATCGCTCCCAATGGCCTCGCCAGTCCC
GCCTCCCACGCCGGATGGGGCTGCTGCAAGACACCTGCAGCCGCCTGCAAATCGCAGTGCTGGCCGTCAG
GGTACCAGTAATACCGCCGTGCGCTCCGCCTCGAGCCCCCTCGACCGCAGGCCAGCCGCGGCGGCGCCGT
CGTCAAGATCCCCCTCGGCCAGCGCCCCCAGCGTGAGGGATCTGAAGAAGCGCTTCGATCAGAACAGCGG
CCCCAACTCCATCCCAAGAGCTCCTCCACGCCAGGCTGCACCGGTGGCCCGGGTCAGCAAGCAAGAGTCC
AGCAAACCCAAGCCCAAGCCCAAGCCCAGCCTGTCGGCCCCTTCGTCCACGCACCCAGGCTCTCGCTCGG
CGGTCCCCGCTTCCAACTCGTCCAAGCAATCTCGGTCGTCGTCGTCGTCCAACTCAGCCTCGACCTCGCG
CTCGACGTCGACGCCGGCCCCGTCAGCCCGCTCGCAGAAGCCACGGCACGTTGAGCGCGAGCAGGCGGCG
GGAAGTTCGCGGTCGTTTGCAAACCGTATTGGGAACCATCAGCCTGAGACATCCACTACTAACGGGAACT
CGAACGCCTCCAGCTCTATGACACCACGCCCACACAAGTCCCCACCCTCAGCCTCCCAGCCGTCGCCGCC
ATCCCCAAAGTCTAATCCTCAGTTCCCGGGCCTCCTGTTTGGCGAAATCCCCCCGGGCCAGCTCGACGTT
GCCGCGCCAGGCTTTGGCATCGACAACATCCGCCCGCGACGAACGTCCGAATCCAACGTGCACGGCCTCG
CGGGGCGTCAACGCAGCCTCTCCGACCTCGAAGCCGAGCCCGCGTCCCCGTCCAGCTGGTACAGGGACGT
CCACATGTCCCGAGGGAGCACGCCGAAAACCCACGCGCGATCTCGCAGCGATCTCTCGGCGCTGAAGCCC
ATCCTCACAACCTTGCATCCCAAGTCGCCTACGCCCGCATCGGCGTCGGCATCAGCAAAGACAAGGGCGA
AATCACCAACAGTAGCTGCTTTCGCGGCAGCCACGGTAACGGCAACGGCTGTCGCAGCAGGGGCCGCGGC
CGCCACCCCTTCGGTCTCGCACGCGTCGGCAGCCGCCAGCTCCAAACTCCCCGTTTCCATCAGCAGGAGG
CTTGCGAGCCCAACCAACTCCAGTCCTACCTCTTCGCGATCAGCCTCGCCCTCTGCGCTTCGCAGACTGC
CAGCCAATGGTCGTAGCAATAGCAGACAGGCCAAACCGATCGCCCCCACGAACCGAGCGAAAACACCCAC
GCAGACGGGTCGAAAGCAGCCTCCCCAGGGGCTCGTTACACCGAGTAATAGCAACAACCGGCTCCAAGCG
TACGTGTCCACCGCACCACCCAAGCTCTCACCGCCATTGAGGAGCTCTCGACCGCGACAGCCAGTCTCCG
TAGCGACGACAGCAAGCTCCCGGATGAAAGAGGCGGCGGCCAAGGCGAAGCCCCCTGCACGGCCAAATGC
ACGGGACGGCCCTTCGTCGTCCAAGACGTACGATCCGGCGAAGCGTAAAATCATAGTGGGACCCATAGAC
TTCGAGCAGCGTCGGGAACACATTCGACTGGCATACACCAAGACCATTCGCGAAAGCCAGGCCTTTGAGG
TGCGCCAGAAAGCGGTGGAGAGGAGGCGGAAGCAGATGGAGGAGGCCAAATCGGAAGCCGCAGCCACCGA
AGCTACAGCGACAAGTAGCACAGCTACAGGCCCATCTACGTCTGCGGATTCACCGACCACGGTGACTGCT
GGAGATGACGAGGCGACGAATAAGGGGCCCTCGGACGGCCATGCACGAGTAATTCCAGAAGTAATAGCGG
CAGAGACAGGGCTGGTCGCGAGCCCCTCGGCACAGGAGCCGGCTGTGGAACTCCCAGCTGATCATGGCTC
TCGCGCTGCTGTGGAGAACCAGGGAACCCTTCTAGAAATCCCGACAGATGCAGCCTCGCACCCGGCATCT
GGCAAGGGTGATGATTCGCCGACGCTGGGCATCCCCGGGGGCTTCCCAGAACCCTCACCGTCCTCCGCCG
CGGCCAGAACGCAGCGGCCTCTGTCGACCATTTCAATCATTTCAGCCACGTCTGCTGTTACGGAGTTTGA
TACAGAGCCCCAGGCGGAGCTCGCCGACCTGGCTATGTCCGATCGGCCGCTCAGCCCCCAGATCATAGTG
CCGACGAGGGAGCGCTCTCAGTATAGAAGCCCCTTTGAGGACGACGATTTCCCATCGTCGCCGCCTCGGC
CGCGTCCTGCGGCCCATCCCCATCAAATCAGCCAAGATCGCCACCATATCGACCAGCCGTTCATCCCTGA
CGCTTATTACGACAATGAGCATCGGGAGCACCCCTTGGAGACCCATGCCCAGCAAGATTACCAAACCATT
GTGACGATTCTGCCGCAGCCCTCACGCGAGCCCCCTGCTGCCGAGGAGACTGCGCAGGCGGCATCTTTTC
CCCGACTAGACATTCAAGATGAATCTGACTGCCACTCGGATCTAGAAAGCGTTCCGGCAATGGCTCGTCG
CATGCGTAGTGATGTCGACGATGCCGCCACTGATGCCTGCACCGAAGAGACGGACGACCGCGATGGGATG
GAGGACGAGCGGTCCCCGTACCGCTATGGCGGCACCCTCTCGTCGAACAGGGCCTCTACATGCGCATCAT
CGGACATAGAAACGTTTGACGACCTTTTGTACCCTTCGCATGACGAGCAGCTGGATGCGGGCCCACCAAA
CAGACTACTGGCGCCGCCCTCGATCTCTCGGGCCGACAGATCGAGCCACCAGACCGCATGGACGAATGTC
TCCGTCGAAAGCATTACGCGCTCCGAGGCTTCAGACTCTCCTGTTCTACGAGCCAGCTCCTGGAAGATGT
CCGGTTCGTCCGGGCGAGACGACTCTTCCCTCAGAAGCCTCCCCTATAGCGGAGTCGGCGTCCGCCCTTC
AGTCGACTCGACGCGGTCGTCGATTCAGCTTGGCCAGCAGCTCCCGGAGCTAGACACGGGCGAAGGCTTC

FIG. 1A

(SEQ ID NO: 1; *Continued*)
TCCATCCCGTATCTGTCCGCAGAGGCAACCTCCGACCTCTCCTACCTCTCTTCCCCCGGGAAACACGAGC
CAGCACCTCACCCGCGCTCTGGACGGAACTCGGCCATCGACTCGCAAACGTCGAGCGTGTTCTATGAGCA
GTCCCAGTATGGCAGCACGTTGGTCAACTCCGATCGCGGGAGTGGAGAATATGTCTCCCACCATTCGGAA
ACTCCTCTGTCGATGATGGACTTGACCTCGATGGAGACTATGGATCGGTACTATGACGGTCGCACCCAGG
TGGATAGCGATGCCAAGTCATTCATCCAAGAATCCGAGGGGCTAAGCAGCGAAGAGCGGCATCGCCTTAT
CCAGAGGCGTAACGTCATCAAGGAGCTTGTGGATACCGAAGCAATTTTTGTAAGAGACATGAACATTGTG
GAGGAAATCTACAAGGGCACCGCAGAGGCGTGCCCCAAGCTGGACACCAAGATTGTCAAGCTCATCTTCA
GGAACAGCGACGAGATTATCGAGTTTCACACCTCGTTCCTCGTCCTCCTCAAAGAGGCAGTGGCCAGCAT
TTACGTACCGAAGGGCGGCCGGTCTCTCGTCGCGAGAGAAGACTCCATCTATTCGGAACAAGGCCAGACT
TCCATCGTCGACCTCAGCGATGCCAAGGACAGAGAGACGTCGCTCGGTCCAACTTTCCAAGCCAACATGG
AGAAGATGAAGCTTGCTCACGAAGGGTTCCTGCGAAACAGCGACCAAGCAGCAAAGAAACTGATCCAGAT
CCAGCAGGACCCGACGGTGCAGATATGGCTGAACGAGTGTAATGAGGTAGCCAAGGACCTGACAGCTGCC
TGGGATCTGGACTCCCTTCTCATCAAGCCGATGCAACGAATCACAAAGTATCCGAATCTGATCATGACGC
TCCTTCAGCACACGCCCCAGGACCACCCCGATCGGGAGGCCCTCGTGATGGCCAAAGAGGCGCTCGAAGA
GGCCATTATCGAGATCAACAAGACGAAGAAGAACTTTGAGCTGGTCGGACAGATCGTCGGTAGAAAACGT
AAGGAGTCCGACGTGAAGGCCGGACTCGCTCGTGCCTTTGGCAAGAAGGTGGACAAGCTGCAAGGCGGAA
CTCGGCCACCGGAGGATCCAGAATATCTCAAGCTGGAGGAAAGGTTCAGCGACGATTACTTGCGGCTACA
GGTCGTCTTGCGCGATGTCGAGTTCTACACCCGGCAAGTCTCATCGTATGTGCACGAGTTCCTGCAGTAC
CTATCAGCCATCGAGCTGGTCATGCGTCTTCAGCCGGGCAGCTTCCCCGAGCTGGAGAGCAAGTGGGTGC
GCTTCAATATCTCCATTCGCGACATTGAGAAGGTAGCGCTCGAGCAGCATgtaagcttcgcaaacctccc
tttcccttgcccccccctaaagcaaattttcctcgcaaaggactatactgactttctattgcaacagCTGT
CACAGATTCGAAAGCATGTCATTGAGCCTTTTGAGCAGGTCATCAAGTCCTACGGGAACCCCTCGCTGGC
TATGAAGAAGAGACAAAAGCGCCGAGTCGTGTGGGAGCGCGCAGAGCAGCTGAAGAAGGCAGGCAAAAGC
GTCGATCCCAAGCTTAAGGAGCTGGTTGAGCAGTATGAAGCTCTCAACGATACGCTAATCAAGGAGCTTC
CCAAGCTTTCGGCGCTGACGGAGAAGGTGGGAAACATTTGTCTCAGCAATCTCATCAACATCCAGGCCAA
TTGGTACTTCATTTGGAGGGAGAAGATGAGAGCTGTGCTGCCGGACTCGCCCACGATGCCAGACATTGAG
GAAATAGTCTCGACTTTCCAGCGAGACTTTCCCTATGCGAACGAGATGATGGCCAGCATCGGCATCATCA
ACCCAGCCTACCGCGGAAGGACATCACAATCAACGAACCACGGAGACGACGCCGGCCTGCCCAGGACTAG
AGGCCGAACCTCAGAGTCGGTAGATAGGGGATGGAGTCAGTCTTTCAACGGCGAAGGCGCACCAAGCCTA
CCGCCTCCCGATTTTGGCAAACGGCATAGCGGCTCGTTTACCCTCTCCCCCATCAGCGCCGGCCCGTCCT
CCTCTGGCTTCGGGACGTCAGCTCCCAGTCCCCACCAGTACTATTATCGTGACTTTTATGCCGGCCTGTC
AAGCAACCAGGCGGGAATGACATCCCCGAGATCGGCCGAGGTACCAGCAACCTCTCGATCGCTCGGAGGC
ACGCGGCCGAGTACGGGCAAAAGCTACGATTCGTCGGCAATCTCAATGCCGAGACAGAGCACGGAGTCGG
CGCCTCACATCCGACGGGACTCGGGCACGGCGTACTATTCCAGCTACCACCAGCACGACAGCCGTAGATT
CTCAAATCTCTTTCACTCTGCCCTTCCTCTACCGGACGGCCCCGAAGAGAGTCAGCGGTCCTCTAGAGCA
TCATCGCGGGAGCGAGCACATGCTTCTGATGGGTACAATATCCTATGGCTGGCAGCGTCGCTCTTCGAGT
TTAACATCTCGACAACCAAGCACGAGGCTGGCTATCCTTATCTGACGTATCAGGCCGGCGAGgtatgttt
ttttttttttctagtatcccagagctcgcaccgtctcttgtggagctagacatgctgacaatgagaatct
tgacagATATTCGATGTAATTGCCGAGAAAGGCGAGCTTTGGCTTGCCAAGAATCAAGACGACCCAACGG
ACCAGGTGGGCTGGATCTGGTCCAAACACTTTGCGAAATTGGCCGACTCATAG

FIG. 1B

(SEQ ID NO: 3)
ATGGACCCGGACCCGGACCTGCACCTGCCAGCACGAGTAGAGCGCGCGAGCCTGGATGGTAGCGTGTTTG
TAGCCCACGATGCGCATCCGCCGGCTCGCCATCTGCCCCATCTCCATCTCCCCCAGCTGGCCCATCCAGC
CTCAAACTCAACCTCCAACTTCACCTTGCGCTCGCACTCGCACTCGCCCGCTGCCGGCGACGTCGTCCTG
CCCGCCTCAACCGCCAATGCCCACGTCCTCGCCCACCATGCAGCTGCCACCCTAGATCCTGACGACTACT
ACAGGAGCTACGAGACAGCCTCCAGCCCCGGCGGCGAGCCACAATCGCTCCCAATGGCCTCGCCAGTCCC
GCCTCCCACGCCGGATGGGGCTGCTGCAAGACACCTGCAGCCGCCTGCAAATCGCAGTGCTGGCCGTCAG
GGTACCAGTAATACCGCCGTGCGCTCCGCCTCGAGCCCCCTCGACCGCAGGCCAGCCGCGGCGGCGCCGT
CGTCAAGATCCCCCTCGGCCAGCGCCCCCAGCGTGAGGGATCTGAAGAAGCGCTTCGATCAGAACAGCGG
CCCCAACTCCATCCCAAGAGCTCCTCCACGCCAGGCTGCACCGGTGGCCCGGGTCAGCAAGCAAGAGTCC
AGCAAACCCAAGCCCAAGCCCAAGCCCAGCCTGTCGGCCCCTTCGTCCACGCACCCAGGCTCTCGCTCGG
CGGTCCCCGCTTCCAACTCGTCCAAGCAATCTCGGTCGTCGTCGTCGTCCAACTCAGCCTCGACCTCGCG
CTCGACGTCGACGCCGGCCCCGTCAGCCCGCTCGCAGAAGCCACGGCACGTTGAGCGCGAGCAGGCGGCG
GGAAGTTCGCGGTCGTTTGCAAACCGTATTGGGAACCATCAGCCTGAGACATCCACTACTAACGGGAACT
CGAACGCCTCCAGCTCTATGACACCACGCCCACACAAGTCCCCACCCTCAGCCTCCCAGCCGTCGCCGCC
ATCCCCAAAGTCTAATCCTCAGTTCCCGGGCCTCCTGTTTGGCGAAATCCCCCCGGGCCAGCTCGACGTT
GCCGCGCCAGGCTTTGGCATCGACAACATCCGCCCGCGACGAACGTCCGAATCCAACGTGCACGGCCTCG
CGGGGCGTCAACGCAGCCTCTCCGACCTCGAAGCCGAGCCCGCGTCCCCGTCCAGCTGGTACAGGGACGT
CCACATGTCCCGAGGGAGCACGCCGAAAACCCACGCGCGATCTCGCAGCGATCTCTCGGCGCTGAAGCCC
ATCCTCACAACCTTGCATCCCAAGTCGCCTACGCCCGCATCGGCGTCGGCATCAGCAAAGACAAGGGCGA
AATCACCAACAGTAGCTGCTTTCGCGGCAGCCACGGTAACGGCAACGGCTGTCGCAGCAGGGGCCGCGGC
CGCCACCCCTTCGGTCTCGCACGCGTCGGCAGCCGCCAGCTCCAAACTCCCCGTTTCCATCAGCAGGAGG
CTTGCGAGCCCAACCAACTCCAGTCCTACCTCTTCGCGATCAGCCTCGCCCTCTGCGCTTCGCAGACTGC
CAGCCAATGGTCGTAGCAATAGCAGACAGGCCAAACCGATCGCCCCCACGAACCGAGCGAAAACACCCAC
GCAGACGGGTCGAAAGCAGCCTCCCCAGGGGCTCGTTACACCGAGTAATAGCAACAACCGGCTCCAAGCG
TACGTGTCCACCGCACCACCCAAGCTCTCACCGCCATTGAGGAGCTCTCGACCGCGACAGCCAGTCTCCG
TAGCGACGACAGCAAGCTCCCGGATGAAAGAGGCGGCGGCCAAGGCGAAGCCCCCTGCACGGCCAAATGC
ACGGGACGGCCCTTCGTCGTCCAAGACGTACGATCCGGCGAAGCGTAAAATCATAGTGGGACCCATAGAC
TTCGAGCAGCGTCGGGAACACATTCGACTGGCATACACCAAGACCATTCGCGAAAGCCAGGCCTTTGAGG
TGCGCCAGAAAGCGGTGGAGAGGAGGCGGAAGCAGATGGAGGAGGCCAAATCGGAAGCCGCAGCCACCGA
AGCTACAGCGACAAGTAGCACAGCTACAGGCCCATCTACGTCTGCGGATTCACCGACCACGGTGACTGCT
GGAGATGACGAGGCGACGAATAAGGGGCCCTCGGACGGCCATGCACGAGTAATTCCAGAAGTAATAGCGG
CAGAGACAGGGCTGGTCGCGAGCCCCTCGGCACAGGAGCCGGCTGTGGAACTCCCAGCTGATCATGGCTC
TCGCGCTGCTGTGGAGAACCAGGGAACCCTTCTAGAAATCCCGACAGATGCAGCCTCGCACCCGGCATCT
GGCAAGGGTGATGATTCGCCGACGCTGGGCATCCCCGGGGGCTTCCCAGAACCCTCACCGTCCTCCGCCG
CGGCCAGAACGCAGCGGCCTCTGTCGACCATTTCAATCATTTCAGCCACGTCTGCTGTTACGGAGTTTGA
TACAGAGCCCCAGGCGGAGCTCGCCGACCTGGCTATGTCCGATCGGCCGCTCAGCCCCCAGATCATAGTG
CCGACGAGGGAGCGCTCTCAGTATAGAAGCCCCTTTGAGGACGACGATTTCCCATCGTCGCCGCCTCGGC
CGCGTCCTGCGGCCCATCCCCATCAAATCAGCCAAGATCGCCACCATATCGACCAGCCGTTCATCCCTGA
CGCTTATTACGACAATGAGCATCGGGAGCACCCCTTGGAGACCCATGCCCAGCAAGATTACCAAACCATT
GTGACGATTCTGCCGCAGCCCTCACGCGAGCCCCCTGCTGCCGAGGAGACTGCGCAGGCGGCATCTTTTC
CCCGACTAGACATTCAAGATGAATCTGACTGCCACTCGGATCTAGAAAGCGTTCCGGCAATGGCTCGTCG
CATGCGTAGTGATGTCGACGATGCCGCCACTGATGCCTGCACCGAAGAGACGGACGACCGCGATGGGATG
GAGGACGAGCGGTCCCCGTACCGCTATGGCGGCACCCTCTCGTCGAACAGGGCCTCTACATGCGCATCAT
CGGACATAGAAACGTTTGACGACCTTTTGTACCCTTCGCATGACGAGCAGCTGGATGCGGGCCCACCAAA
CAGACTACTGGCGCCGCCCTCGATCTCTCGGGCCGACAGATCGAGCCACCAGACCGCATGGACGAATGTC

FIG. 2A

(SEQ ID NO: 3; *Continued*)
TCCGTCGAAAGCATTACGCGCTCCGAGGCTTCAGACTCTCCTGTTCTACGAGCCAGCTCCTGGAAGATGT
CCGGTTCGTCCGGGCGAGACGACTCTTCCCTCAGAAGCCTCCCCTATAGCGGAGTCGGCGTCCGCCCTTC
AGTCGACTCGACGCGGTCGTCGATTCAGCTTGGCCAGCAGCTCCCGGAGCTAGACACGGGCGAAGGCTTC
TCCATCCCGTATCTGTCCGCAGAGGCAACCTCCGACCTCTCCTACCTCTCTTCCCCCGGGAAACACGAGC
CAGCACCTCACCCGCGCTCTGGACGGAACTCGGCCATCGACTCGCAAACGTCGAGCGTGTTCTATGAGCA
GTCCCAGTATGGCAGCACGTTGGTCAACTCCGATCGCGGGAGTGGAGAATATGTCTCCCACCATTCGGAA
ACTCCTCTGTCGATGATGGACTTGACCTCGATGGAGACTATGGATCGGTACTATGACGGTCGCACCCAGG
TGGATAGCGATGCCAAGTCATTCATCCAAGAATCCGAGGGGCTAAGCAGCGAAGAGCGGCATCGCCTTAT
CCAGAGGCGTAACGTCATCAAGGAGCTTGTGGATACCGAAGCAATTTTTGTAAGAGACATGAACATTGTG
GAGGAAATCTACAAGGGCACCGCAGAGGCGTGCCCCAAGCTGGACACCAAGATTGTCAAGCTCATCTTCA
GGAACAGCGACGAGATTATCGAGTTTCACACCTCGTTCCTCGTCCTCCTCAAAGAGGCAGTGGCCAGCAT
TTACGTACCGAAGGGCGGCCGGTCTCTCGTCGCGAGAGAAGACTCCATCTATTCGGAACAAGGCCAGACT
TCCATCGTCGACCTCAGCGATGCCAAGGACAGAGAGACGTCGCTCGGTCCAACTTTCCAAGCCAACATGG
AGAAGATGAAGCTTGCTCACGAAGGGTTCCTGCGAAACAGCGACCAAGCAGCAAAGAAACTGATCCAGAT
CCAGCAGGACCCGACGGTGCAGATATGGCTGAACGAGTGTAATGAGGTAGCCAAGGACCTGACAGCTGCC
TGGGATCTGGACTCCCTTCTCATCAAGCCGATGCAACGAATCACAAAGTATCCGAATCTGATCATGACGC
TCCTTCAGCACACGCCCCAGGACCACCCCGATCGGGAGGCCCTCGTGATGGCCAAAGAGGCGCTCGAAGA
GGCCATTATCGAGATCAACAAGACGAAGAAGAACTTTGAGCTGGTCGGACAGATCGTCGGTAGAAAACGT
AAGGAGTCCGACGTGAAGGCCGGACTCGCTCGTGCCTTTGGCAAGAAGGTGGACAAGCTGCAAGGCGGAA
CTCGGCCACCGGAGGATCCAGAATATCTCAAGCTGGAGGAAAGGTTCAGCGACGATTACTTGCGGCTACA
GGTCGTCTTGCGCGATGTCGAGTTCTACACCCGGCAAGTCTCATCGTATGTGCACGAGTTCCTGCAGTAC
CTATCAGCCATCGAGCTGGTCATGCGTCTTCAGCCGGGCAGCTTCCCCGAGCTGGAGAGCAAGTGGGTGC
GCTTCAATATCTCCATTCGCGACATTGAGAAGGTAGCGCTCGAGCAGCATCTGTCACAGATTCGAAAGCA
TGTCATTGAGCCTTTTGAGCAGGTCATCAAGTCCTACGGGAACCCCTCGCTGGCTATGAAGAAGAGACAA
AAGCGCCGAGTCGTGTGGGAGCGCGCAGAGCAGCTGAAGAAGGCAGGCAAAAGCGTCGATCCCAAGCTTA
AGGAGCTGGTTGAGCAGTATGAAGCTCTCAACGATACGCTAATCAAGGAGCTTCCCAAGCTTTCGGCGCT
GACGGAGAAGGTGGGAAACATTTGTCTCAGCAATCTCATCAACATCCAGGCCAATTGGTACTTCATTTGG
AGGGAGAAGATGAGAGCTGTGCTGCCGGACTCGCCCACGATGCCAGACATTGAGGAAATAGTCTCGACTT
TCCAGCGAGACTTTCCCTATGCGAACGAGATGATGGCCAGCATCGGCATCATCAACCCAGCCTACCGCGG
AAGGACATCACAATCAACGAACCACGGAGACGACGCCGGCCTGCCCAGGACTAGAGGCCGAACCTCAGAG
TCGGTAGATAGGGGATGGAGTCAGTCTTTCAACGGCGAAGGCGCACCAAGCCTACCGCCTCCCGATTTTG
GCAAACGGCATAGCGGCTCGTTTACCCTCTCCCCCATCAGCGCCGGCCCGTCCTCCTCTGGCTTCGGGAC
GTCAGCTCCCAGTCCCCACCAGTACTATTATCGTGACTTTTATGCCGGCCTGTCAAGCAACCAGGCGGGA
ATGACATCCCCGAGATCGGCCGAGGTACCAGCAACCTCTCGATCGCTCGGAGGCACGCGGCCGAGTACGG
GCAAAAGCTACGATTCGTCGGCAATCTCAATGCCGAGACAGAGCACGGAGTCGGCGCCTCACATCCGACG
GGACTCGGGCACGGCGTACTATTCCAGCTACCACCAGCACGACAGCCGTAGATTCTCAAATCTCTTTCAC
TCTGCCCTTCCTCTACCGGACGGCCCCGAAGAGAGTCAGCGGTCCTCTAGAGCATCATCGCGGGAGCGAG
CACATGCTTCTGATGGGTACAATATCCTATGGCTGGCAGCGTCGCTCTTCGAGTTTAACATCTCGACAAC
CAAGCACGAGGCTGGCTATCCTTATCTGACGTATCAGGCCGGCGAGATATTCGATGTAATTGCCGAGAAA
GGCGAGCTTTGGCTTGCCAAGAATCAAGACGACCCAACGGACCAGGTGGGCTGGATCTGGTCCAAACACT
TTGCGAAATTGGCCGACTCATAG

FIG. 2B

(SEQ ID NO: 2; Native RhoGEF)

MDPDPDLHLPARVERASLDGSVFVAHDAHPPARHLPHLHLPQLAHPASNSTSNFTLRSHSHSPAAGDVVLPASTANA
HVLAHHAAATLDPDDYYRSYETASSPGGEPQSLPMASPVPPPTPDGAAARHLQPPANRSAGRQGTSNTAVRSASSPL
DRRPAAAAPSSRSPSASAPSVRDLKKRFDQNSGPNSIPRAPPRQAAPVARVSKQESSKPKPKPKPSLSAPSSTHPGS
RSAVPASNSSKQSRSSSSSNSASTSRSTSTPAPSARSQKPRHVEREQAAGSSRSFANRIGNHQPETSTTNGNSNASS
SMTPRPHKSPPSASQPSPPSPKSNPQFPGLLFGEIPPGQLDVAAPGFGIDNIRPRRTSESNVHGLAGRQRSLSDLEA
EPASPSSWYRDVHMSRGSTPKTHARSRSDLSALKPILTTLHPKSPTPASASASAKTRAKSPTVAAFAAATVTATAVA
AGAAAATPSVSHASAAASSKLPVSISRRLASPTNSSPTSSRSASPSALRRLPANGRSNSRQAKPIAPTNRAKTPTQT
GRKQPPQGLVTPSNSNNRLQAYVSTAPPKLSPPLRSSRPRQPVSVATTASSRMKEAAAKAKPPARPNARDGPSSSKT
YDPAKRKIIVGPIDFEQRREHIRLAYTKTIRESQAFEVRQKAVERRRKQMEEAKSEAAATEATATSSTATGPSTSAD
SPTTVTAGDDEATNKGPSDGHARVIPEVIAAETGLVASPSAQEPAVELPADHGSRAAVENQGTLLEIPTDAASHPAS
GKGDDSPTLGIPGGFPEPSPSSAAARTQRPLSTISIISATSAVTEFDTEPQAELADLAMSDRPLSPQIIVPTRERSQ
YRSPFEDDDFPSSPPRPRPAAHPHQISQDRHHIDQPFIPDAYYDNEHREHPLETHAQQDYQTIVTILPQPSREPPAA
EETAQAASFPRLDIQDESDCHSDLESVPAMARRMRSDVDDAATDACTEETDDRDGMEDERSPYRYGGTLSSNRASTC
ASSDIETFDDLLYPSHDEQLDAGPPNRLLAPPSISRADRSSHQTAWTNVSVESITRSEASDSPVLRASSWKMSGSSG
RDDSSLRSLPYSGVGVRPSVDSTRSSIQLGQQLPELDTGEGFSIPYLSAEATSDLSYLSSPGKHEPAPHPRSGRNSA
IDSQTSSVFYEQSQYGSTLVNSDRGSGEYVSHHSETPLSMMDLTSMETMDRYYDGRTQVDSDAKSFIQESEGLSSEE
RHRLIQRRNVIEELVDTEAIFVRDMNIVEEIYKGTAEACPKLDTKIVKLIFRNSDEIIEFHTSFLVLLKEAVASIYV
PKGGRSLVAREDSIYSEQGQTSIVDLSDAKDRETSLGPTFQANMEKMKLAHEGFLRNSDQAAKKLIQIQQDPTVQIW
LNECNEVAKDLTAAWDLDSLLIKPMQRITKYPNLIMTLLQHTPQDHPDREALVMAKEALEEAIIEINKTKKNFELVG
QIVGRKRKESDVKAGLARAFGKKVDKLQGGTRPPEDPEYLKLEERFSDDYLRLQVVLRDVEFYTRQVSSYVHEFLQY
LSAIELVMRLQPGSFPELESKWVRFNISIRDIEKVALEQHLSQIRKHVIEPFEQVIKSYGNPSLAMKKRQKRRVVWE
RAEQLKKAGKSVDPKLKELVEQYEALNDTLIKELPKLSALTEKVGNICLSNLINIQANWYFIWREKMRAVLPDSPTM
PDIEEIVSTFQRDFPYANEMMASIGIINPAYRGRTSQSTNHGDDAGLPRTRGRTSESVDRGWSQSFNGEGAPSLPPP
DFGKRHSGSFTLSPISAGPSSSGFGTSAPSPHQYYYRDFYAGLSSNQAGMTSPRSAEVPATSRSLGGTRPSTGKSYD
SSAISMPRQSTESAPHIRRDSGTAYYSSYHQHDSRRFSNLFHSALPLPDGPEESQRSSRASSRERAHASD*GYNILWL*
*AASLFEFNISTTKHEAGYPYLTYQAGEIFDVIAEKGELWLAKNQDDPTDQVGWIWSKHFAKLADS*

FIG. 3A

(SEQ ID NO: 4; Variant RhoGEF with C-terminal truncation)

MDPDPDLHLPARVERASLDGSVFVAHDAHPPARHLPHLHLPQLAHPASNSTSNFTLRSHSHSPAAGDVVLPASTANA
HVLAHHAAATLDPDDYYRSYETASSPGGEPQSLPMASPVPPPTPDGAAARHLQPPANRSAGRQGTSNTAVRSASSPL
DRRPAAAAPSSRSPSASAPSVRDLKKRFDQNSGPNSIPRAPPRQAAPVARVSKQESSKPKPKPKPSLSAPSSTHPGS
RSAVPASNSSKQSRSSSSSNSASTSRSTSTPAPSARSQKPRHVEREQAAGSSRSFANRIGNHQPETSTTNGNSNASS
SMTPRPHKSPPSASQPSPPSPKSNPQFPGLLFGEIPPGQLDVAAPGFGIDNIRPRRTSESNVHGLAGRQRSLSDLEA
EPASPSSWYRDVHMSRGSTPKTHARSRSDLSALKPILTTLHPKSPTPASASASAKTRAKSPTVAAFAAATVTATAVA
AGAAAATPSVSHASAAASSKLPVSISRRLASPTNSSPTSSRSASPSALRRLPANGRSNSRQAKPIAPTNRAKTPTQT
GRKQPPQGLVTPSNSNNRLQAYVSTAPPKLSPPLRSSRPRQPVSVATTASSRMKEAAAKAKPPARPNARDGPSSSKT
YDPAKRKIIVGPIDFEQRREHIRLAYTKTIRESQAFEVRQKAVERRRKQMEEAKSEAAATEATATSSTATGPSTSAD
SPTTVTAGDDEATNKGPSDGHARVIPEVIAAETGLVASPSAQEPAVELPADHGSRAAVENQGTLLEIPTDAASHPAS
GKGDDSPTLGIPGGFPEPSPSSAAARTQRPLSTISIISATSAVTEFDTEPQAELADLAMSDRPLSPQIIVPTRERSQ
YRSPFEDDDFPSSPPRPRPAAHPHQISQDRHHIDQPFIPDAYYDNEHREHPLETHAQQDYQTIVTILPQPSREPPAA
EETAQAASFPRLDIQDESDCHSDLESVPAMARRMRSDVDDAATDACTEETDDRDGMEDERSPYRYGGTLSSNRASTC
ASSDIETFDDLLYPSHDEQLDAGPPNRLLAPPSISRADRSSHQTAWTNVSVESITRSEASDSPVLRASSWKMSGSSG
RDDSSLRSLPYSGVGVRPSVDSTRSSIQLGQQLPELDTGEGFSIPYLSAEATSDLSYLSSPGKHEPAPHPRSGRNSA
IDSQTSSVFYEQSQYGSTLVNSDRGSGEYVSHHSETPLSMMDLTSMETMDRYYDGRTQVDSDAKSFIQESEGLSSEE
RHRLIQRRNVIK

FIG. 3B

(SEQ ID NO: 5; RhoGEF Domain)
VIEELVDTEAIFVRDMNIVEEIYKGTAEACPKLDTKIVKLIFRNSDEIIEFHTSFLVLLKEAVASIYVPKGGRSLVA
REDSIYSEQGQTSIVDLSDAKDRETSLGPTFQANMEKMKLAHEGFLRNSDQAAKKLIQIQQDPTVQIWLNECNEVAK
DLTAAWDLDSLLIKPMQRITKYPNLIMTLLQHTPQDHPDREALVMAKEALEEAIIEINK

FIG. 3C

(SEQ ID NO: 6; BAR Domain)
ALEQHLSQIRKHVIEPFEQVIKSYGNPSLAMKKRQKRRVVWERAEQLKKAGKSVDPKLKELVEQYEALNDTLIKELP
KLSALTEKVGNICLSNLINIQANWY

FIG. 3D

(SEQ ID NO: 7; Unknown Domain)
GYNILWLAASLFEFNISTTKHEAGYPYLTYQAGEIFDVIAEKGELWLAKNQDDPTDQVGWIWSKHFAKLADS

FIG. 3E

SEQUENCE LISTING

<160> NUMBER OF SEQ ID NOS: 19

<210> SEQ ID NO 1
<211> LENGTH: 6143
<212> TYPE: DNA
<213> ORGANISM: Hypocrea jecorina

<400> SEQUENCE: 1
atggacccgg acccggacct gcacctgcca gcacgagtag agcgcgcgag cctggatggt 60
agcgtgtttg tagcccacga tgcgcatccg ccggctcgcc atctgcccca tctccatctc 120
ccccagctgg cccatccagc ctcaaactca acctccaact tcaccttgcg ctcgcactcg 180
cactcgcccg ctgccggcga cgtcgtcctg cccgcctcaa ccgccaatgc ccacgtcctc 240
gcccaccatg cagctgccac cctagatcct gacgactact acaggagcta cgagacagcc 300
tccagccccg gcggcgagcc acaatcgctc ccaatggcct cgccagtccc gcctcccacg 360
ccggatgggg ctgctgcaag acacctgcag ccgcctgcaa atcgcagtgc tggccgtcag 420
ggtaccagta ataccgccgt gcgctccgcc tcgagccccc tcgaccgcag gccagccgcg 480
gcggcgccgt cgtcaagatc cccctcggcc agcgccccca gcgtgaggga tctgaagaag 540
cgcttcgatc agaacagcgg ccccaactcc atcccaagag ctcctccacg ccaggctgca 600
ccggtggccc gggtcagcaa gcaagagtcc agcaaaccca agcccaagcc caagcccagc 660
ctgtcggccc cttcgtccac gcacccaggc tctcgctcgg cggtccccgc ttccaactcg 720
tccaagcaat ctcggtcgtc gtcgtcgtcc aactcagcct cgacctcgcg ctcgacgtcg 780
acgccggccc cgtcagcccg ctcgcagaag ccacggcacg ttgagcgcga gcaggcggcg 840
ggaagttcgc ggtcgtttgc aaaccgtatt gggaaccatc agcctgagac atccactact 900
aacgggaact cgaacgcctc cagctctatg acaccacgcc cacacaagtc cccaccctca 960
gcctcccagc cgtcgccgcc atccccaaag tctaatcctc agttcccggg cctcctgttt 1020
ggcgaaatcc ccccgggcca gctcgacgtt gccgcgccag gctttggcat cgacaacatc 1080
cgcccgcgac gaacgtccga atccaacgtg cacggcctcg cggggcgtca acgcagcctc 1140
tccgacctcg aagccgagcc cgcgtccccg tccagctggt acagggacgt ccacatgtcc 1200
cgagggagca cgccgaaaac ccacgcgcga tctcgcagcg atctctcggc gctgaagccc 1260
atcctcacaa ccttgcatcc caagtcgcct acgcccgcat cggcgtcggc atcagcaaag 1320
acaagggcga aatcaccaac agtagctgct ttcgcggcag ccacggtaac ggcaacggct 1380
gtcgcagcag gggccgcggc cgccacccct tcggtctcgc acgcgtcggc agccgccagc 1440

```
tccaaactcc ccgtttccat cagcaggagg cttgcgagcc caaccaactc cagtcctacc   1500
tcttcgcgat cagcctcgcc ctctgcgctt cgcagactgc cagccaatgg tcgtagcaat   1560
agcagacagg ccaaaccgat cgccccccacg aaccgagcga aaacacccac gcagacgggt   1620
cgaaagcagc ctccccaggg gctcgttaca ccgagtaata gcaacaaccg gctccaagcg   1680
tacgtgtcca ccgcaccacc caagctctca ccgccattga ggagctctcg accgcgacag   1740
ccagtctccg tagcgacgac agcaagctcc cggatgaaag aggcggcggc caaggcgaag   1800
ccccctgcac ggccaaatgc acgggacggc ccttcgtcgt ccaagacgta cgatccggcg   1860
aagcgtaaaa tcatagtggg acccatagac ttcgagcagc gtcgggaaca cattcgactg   1920
gcatacacca agaccattcg cgaaagccag gcctttgagg tgcgccagaa agcggtggag   1980
aggaggcgga agcagatgga ggaggccaaa tcggaagccg cagccaccga agctacagcg   2040
acaagtagca cagctacagg cccatctacg tctgcggatt caccgaccac ggtgactgct   2100
ggagatgacg aggcgacgaa taaggggccc tcggacggcc atgcacgagt aattccagaa   2160
gtaatagcgg cagagacagg gctggtcgcg agcccctcgg cacaggagcc ggctgtggaa   2220
ctcccagctg atcatggctc tcgcgctgct gtggagaacc agggaaccct tctagaaatc   2280
ccgacagatg cagcctcgca cccggcatct ggcaagggtg atgattcgcc gacgctgggc   2340
atccccgggg gcttcccaga accctcaccg tcctccgccg cggccagaac gcagcggcct   2400
ctgtcgacca tttcaatcat ttcagccacg tctgctgtta cggagtttga tacagagccc   2460
caggcggagc tcgccgacct ggctatgtcc gatcggccgc tcagccccca gatcatagtg   2520
ccgacgaggg agcgctctca gtatagaagc ccctttgagg acgacgattt cccatcgtcg   2580
ccgcctcggc cgcgtcctgc ggcccatccc catcaaatca gccaagatcg ccaccatatc   2640
gaccagccgt tcatccctga cgcttattac gacaatgagc atcgggagca ccccttggag   2700
acccatgccc agcaagatta ccaaaccatt gtgacgattc tgccgcagcc ctcacgcgag   2760
ccccctgctg ccgaggagac tgcgcaggcg gcatcttttc cccgactaga cattcaagat   2820
gaatctgact gccactcgga tctagaaagc gttccggcaa tggctcgtcg catgcgtagt   2880
gatgtcgacg atgccgccac tgatgcctgc accgaagaga cggacgaccg cgatgggatg   2940
gaggacgagc ggtccccgta ccgctatggc ggcaccctct cgtcgaacag ggcctctaca   3000
tgcgcatcat cggacataga aacgtttgac gaccttttgt acccttcgca tgacgagcag   3060
ctggatgcgg gcccaccaaa cagactactg gcgccgccct cgatctctcg ggccgacaga   3120
tcgagccacc agaccgcatg gacgaatgtc tccgtcgaaa gcattacgcg ctccgaggct   3180
tcagactctc ctgttctacg agccagctcc tggaagatgt ccggttcgtc cgggcgagac   3240
gactcttccc tcagaagcct cccctatagc ggagtcggcg tccgcccttc agtcgactcg   3300
acgcggtcgt cgattcagct tggccagcag ctcccggagc tagacacggg cgaaggcttc   3360
tccatcccgt atctgtccgc agaggcaacc tccgacctct cctacctctc ttcccccggg   3420
aaacacgagc cagcacctca cccgcgctct ggacggaact cggccatcga ctcgcaaacg   3480
tcgagcgtgt tctatgagca gtcccagtat ggcagcacgt tggtcaactc cgatcgcggg   3540
agtggagaat atgtctccca ccattcggaa actcctctgt cgatgatgga cttgacctcg   3600
atggagacta tggatcggta ctatgacggt cgcacccagg tggatagcga tgccaagtca   3660
ttcatccaag aatccgaggg gctaagcagc gaagagcggc atcgccttat ccagaggcgt   3720
aacgtcatca aggagcttgt ggataccgaa gcaatttttg taagagacat gaacattgtg   3780
gaggaaatct acaagggcac cgcagaggcg tgccccaagc tggacaccaa gattgtcaag   3840
```

```
ctcatcttca ggaacagcga cgagattatc gagtttcaca cctcgttcct cgtcctcctc   3900
aaagaggcag tggccagcat ttacgtaccg aagggcggcc ggtctctcgt cgcgagagaa   3960
gactccatct attcggaaca aggccagact tccatcgtcg acctcagcga tgccaaggac   4020
agagagacgt cgctcggtcc aactttccaa gccaacatgg agaagatgaa gcttgctcac   4080
gaagggttcc tgcgaaacag cgaccaagca gcaaagaaac tgatccagat ccagcaggac   4140
ccgacggtgc agatatggct gaacgagtgt aatgaggtag ccaaggacct gacagctgcc   4200
tgggatctgg actcccttct catcaagccg atgcaacgaa tcacaaagta tccgaatctg   4260
atcatgacgc tccttcagca cacgccccag gaccaccccg atcgggaggc cctcgtgatg   4320
gccaaagagg cgctcgaaga ggccattatc gagatcaaca agacgaagaa gaactttgag   4380
ctggtcggac agatcgtcgg tagaaaacgt aaggagtccg acgtgaaggc cggactcgct   4440
cgtgcctttg gcaagaaggt ggacaagctg caaggcggaa ctcggccacc ggaggatcca   4500
gaatatctca agctggagga aaggttcagc gacgattact tgcggctaca ggtcgtcttg   4560
cgcgatgtcg agttctacac ccggcaagtc tcatcgtatg tgcacgagtt cctgcagtac   4620
ctatcagcca tcgagctggt catgcgtctt cagccgggca gcttccccga gctggagagc   4680
aagtgggtgc gcttcaatat ctccattcgc gacattgaga aggtagcgct cgagcagcat   4740
gtaagcttcg caaacctccc tttcccttgc ccccctaaa gcaaattttc ctcgcaaagg   4800
actatactga ctttctattg caacagctgt cacagattcg aaagcatgtc attgagcctt   4860
ttgagcaggt catcaagtcc tacgggaacc cctcgctggc tatgaagaag agacaaaagc   4920
gccgagtcgt gtgggagcgc gcagagcagc tgaagaaggc aggcaaaagc gtcgatccca   4980
agcttaagga gctggttgag cagtatgaag ctctcaacga tacgctaatc aaggagcttc   5040
ccaagctttc ggcgctgacg gagaaggtgg gaaacatttg tctcagcaat ctcatcaaca   5100
tccaggccaa ttggtacttc atttggaggg agaagatgag agctgtgctg ccggactcgc   5160
ccacgatgcc agacattgag gaaatagtct cgactttcca gcgagacttt ccctatgcga   5220
acgagatgat ggccagcatc ggcatcatca acccagccta ccgcggaagg acatcacaat   5280
caacgaacca cggagacgac gccggcctgc ccaggactag aggccgaacc tcagagtcgg   5340
tagatagggg atggagtcag tctttcaacg gcgaaggcgc accaagccta ccgcctcccg   5400
attttggcaa acggcatagc ggctcgttta ccctctcccc catcagcgcc ggcccgtcct   5460
cctctggctt cgggacgtca gctcccagtc cccaccagta ctattatcgt gacttttatg   5520
ccggcctgtc aagcaaccag gcgggaatga catccccgag atcggccgag gtaccagcaa   5580
cctctcgatc gctcggaggc acgcggccga gtacgggcaa aagctacgat tcgtcggcaa   5640
tctcaatgcc gagacagagc acggagtcgg cgcctcacat ccgacgggac tcgggcacgg   5700
cgtactattc cagctaccac cagcacgaca gccgtagatt ctcaaatctc tttcactctg   5760
cccttcctct accggacggc cccgaagaga gtcagcggtc ctctagagca tcatcgcggg   5820
agcgagcaca tgcttctgat gggtacaata tcctatggct ggcagcgtcg ctcttcgagt   5880
ttaacatctc gacaaccaag cacgaggctg gctatcctta tctgacgtat caggccggcg   5940
aggtatgttt tttttttttt ctagtatccc agagctcgca ccgtctcttg tggagctaga   6000
catgctgaca atgagaatct tgacagatat tcgatgtaat tgccgagaaa ggcgagcttt   6060
ggcttgccaa gaatcaagac gacccaacgg accaggtggg ctggatctgg tccaaacact   6120
ttgcgaaatt ggccgactca tag                                           6143
```

<210> SEQ ID NO 2
<211> LENGTH: 1990
<212> TYPE: PRT
<213> ORGANISM: Hypocrea jecorina

<400> SEQUENCE: 2

```
Met Asp Pro Asp Pro Asp Leu His Leu Pro Ala Arg Val Glu Arg Ala
1               5                   10                  15

Ser Leu Asp Gly Ser Val Phe Val Ala His Asp Ala His Pro Pro Ala
            20                  25                  30

Arg His Leu Pro His Leu His Leu Pro Gln Leu Ala His Pro Ala Ser
        35                  40                  45

Asn Ser Thr Ser Asn Phe Thr Leu Arg Ser His Ser His Ser Pro Ala
    50                  55                  60

Ala Gly Asp Val Val Leu Pro Ala Ser Thr Ala Asn Ala His Val Leu
65                  70                  75                  80

Ala His His Ala Ala Ala Thr Leu Asp Pro Asp Asp Tyr Tyr Arg Ser
                85                  90                  95

Tyr Glu Thr Ala Ser Ser Pro Gly Gly Glu Pro Gln Ser Leu Pro Met
            100                 105                 110

Ala Ser Pro Val Pro Pro Pro Thr Pro Asp Gly Ala Ala Ala Arg His
        115                 120                 125

Leu Gln Pro Pro Ala Asn Arg Ser Ala Gly Arg Gln Gly Thr Ser Asn
    130                 135                 140

Thr Ala Val Arg Ser Ala Ser Ser Pro Leu Asp Arg Arg Pro Ala Ala
145                 150                 155                 160

Ala Ala Pro Ser Ser Arg Ser Pro Ser Ala Ser Ala Pro Ser Val Arg
                165                 170                 175

Asp Leu Lys Lys Arg Phe Asp Gln Asn Ser Gly Pro Asn Ser Ile Pro
            180                 185                 190

Arg Ala Pro Pro Arg Gln Ala Ala Pro Val Ala Arg Val Ser Lys Gln
        195                 200                 205

Glu Ser Ser Lys Pro Lys Pro Lys Pro Lys Pro Ser Leu Ser Ala Pro
    210                 215                 220

Ser Ser Thr His Pro Gly Ser Arg Ser Ala Val Pro Ala Ser Asn Ser
225                 230                 235                 240

Ser Lys Gln Ser Arg Ser Ser Ser Ser Ser Asn Ser Ala Ser Thr Ser
                245                 250                 255

Arg Ser Thr Ser Thr Pro Ala Pro Ser Ala Arg Ser Gln Lys Pro Arg
            260                 265                 270

His Val Glu Arg Glu Gln Ala Ala Gly Ser Ser Arg Ser Phe Ala Asn
        275                 280                 285

Arg Ile Gly Asn His Gln Pro Glu Thr Ser Thr Thr Asn Gly Asn Ser
    290                 295                 300

Asn Ala Ser Ser Ser Met Thr Pro Arg Pro His Lys Ser Pro Pro Ser
305                 310                 315                 320

Ala Ser Gln Pro Ser Pro Pro Ser Pro Lys Ser Asn Pro Gln Phe Pro
                325                 330                 335

Gly Leu Leu Phe Gly Glu Ile Pro Pro Gly Gln Leu Asp Val Ala Ala
            340                 345                 350

Pro Gly Phe Gly Ile Asp Asn Ile Arg Pro Arg Arg Thr Ser Glu Ser
        355                 360                 365

Asn Val His Gly Leu Ala Gly Arg Gln Arg Ser Leu Ser Asp Leu Glu
    370                 375                 380
```

```
Ala Glu Pro Ala Ser Pro Ser Ser Trp Tyr Arg Asp Val His Met Ser
385                 390                 395                 400

Arg Gly Ser Thr Pro Lys Thr His Ala Arg Ser Arg Ser Asp Leu Ser
                405                 410                 415

Ala Leu Lys Pro Ile Leu Thr Thr Leu His Pro Lys Ser Pro Thr Pro
            420                 425                 430

Ala Ser Ala Ser Ala Ser Ala Lys Thr Arg Ala Lys Ser Pro Thr Val
        435                 440                 445

Ala Ala Phe Ala Ala Ala Thr Val Thr Ala Thr Ala Val Ala Ala Gly
    450                 455                 460

Ala Ala Ala Ala Thr Pro Ser Val Ser His Ala Ser Ala Ala Ala Ser
465                 470                 475                 480

Ser Lys Leu Pro Val Ser Ile Ser Arg Arg Leu Ala Ser Pro Thr Asn
                485                 490                 495

Ser Ser Pro Thr Ser Ser Arg Ser Ala Ser Pro Ser Ala Leu Arg Arg
            500                 505                 510

Leu Pro Ala Asn Gly Arg Ser Asn Ser Arg Gln Ala Lys Pro Ile Ala
        515                 520                 525

Pro Thr Asn Arg Ala Lys Thr Pro Thr Gln Thr Gly Arg Lys Gln Pro
    530                 535                 540

Pro Gln Gly Leu Val Thr Pro Ser Asn Ser Asn Asn Arg Leu Gln Ala
545                 550                 555                 560

Tyr Val Ser Thr Ala Pro Pro Lys Leu Ser Pro Pro Leu Arg Ser Ser
                565                 570                 575

Arg Pro Arg Gln Pro Val Ser Val Ala Thr Thr Ala Ser Ser Arg Met
            580                 585                 590

Lys Glu Ala Ala Ala Lys Ala Lys Pro Pro Ala Arg Pro Asn Ala Arg
        595                 600                 605

Asp Gly Pro Ser Ser Ser Lys Thr Tyr Asp Pro Ala Lys Arg Lys Ile
    610                 615                 620

Ile Val Gly Pro Ile Asp Phe Glu Gln Arg Arg Glu His Ile Arg Leu
625                 630                 635                 640

Ala Tyr Thr Lys Thr Ile Arg Glu Ser Gln Ala Phe Glu Val Arg Gln
                645                 650                 655

Lys Ala Val Glu Arg Arg Arg Lys Gln Met Glu Glu Ala Lys Ser Glu
            660                 665                 670

Ala Ala Ala Thr Glu Ala Thr Ala Thr Ser Ser Thr Ala Thr Gly Pro
        675                 680                 685

Ser Thr Ser Ala Asp Ser Pro Thr Thr Val Thr Ala Gly Asp Asp Glu
    690                 695                 700

Ala Thr Asn Lys Gly Pro Ser Asp Gly His Ala Arg Val Ile Pro Glu
705                 710                 715                 720

Val Ile Ala Ala Glu Thr Gly Leu Val Ala Ser Pro Ser Ala Gln Glu
                725                 730                 735

Pro Ala Val Glu Leu Pro Ala Asp His Gly Ser Arg Ala Ala Val Glu
            740                 745                 750

Asn Gln Gly Thr Leu Leu Glu Ile Pro Thr Asp Ala Ala Ser His Pro
        755                 760                 765

Ala Ser Gly Lys Gly Asp Asp Ser Pro Thr Leu Gly Ile Pro Gly Gly
    770                 775                 780

Phe Pro Glu Pro Ser Pro Ser Ser Ala Ala Ala Arg Thr Gln Arg Pro
785                 790                 795                 800
```

-continued

```
Leu Ser Thr Ile Ser Ile Ile Ser Ala Thr Ser Ala Val Thr Glu Phe
                805                 810                 815

Asp Thr Glu Pro Gln Ala Glu Leu Ala Asp Leu Ala Met Ser Asp Arg
            820                 825                 830

Pro Leu Ser Pro Gln Ile Ile Val Pro Thr Arg Glu Arg Ser Gln Tyr
        835                 840                 845

Arg Ser Pro Phe Glu Asp Asp Asp Phe Pro Ser Ser Pro Pro Arg Pro
    850                 855                 860

Arg Pro Ala Ala His Pro His Gln Ile Ser Gln Asp Arg His His Ile
865                 870                 875                 880

Asp Gln Pro Phe Ile Pro Asp Ala Tyr Tyr Asp Asn Glu His Arg Glu
                885                 890                 895

His Pro Leu Glu Thr His Ala Gln Gln Asp Tyr Gln Thr Ile Val Thr
            900                 905                 910

Ile Leu Pro Gln Pro Ser Arg Glu Pro Pro Ala Ala Glu Glu Thr Ala
        915                 920                 925

Gln Ala Ala Ser Phe Pro Arg Leu Asp Ile Gln Asp Glu Ser Asp Cys
    930                 935                 940

His Ser Asp Leu Glu Ser Val Pro Ala Met Ala Arg Arg Met Arg Ser
945                 950                 955                 960

Asp Val Asp Asp Ala Ala Thr Asp Ala Cys Thr Glu Glu Thr Asp Asp
                965                 970                 975

Arg Asp Gly Met Glu Asp Glu Arg Ser Pro Tyr Arg Tyr Gly Gly Thr
            980                 985                 990

Leu Ser Ser Asn Arg Ala Ser Thr  Cys Ala Ser Ser Asp  Ile Glu Thr
        995                 1000                1005

Phe Asp  Asp Leu Leu Tyr Pro  Ser His Asp Glu Gln  Leu Asp Ala
    1010                1015                1020

Gly Pro  Pro Asn Arg Leu Leu  Ala Pro Pro Ser Ile  Ser Arg Ala
    1025                1030                1035

Asp Arg  Ser Ser His Gln Thr  Ala Trp Thr Asn Val  Ser Val Glu
    1040                1045                1050

Ser Ile  Thr Arg Ser Glu Ala  Ser Asp Ser Pro Val  Leu Arg Ala
    1055                1060                1065

Ser Ser  Trp Lys Met Ser Gly  Ser Ser Gly Arg Asp  Asp Ser Ser
    1070                1075                1080

Leu Arg  Ser Leu Pro Tyr Ser  Gly Val Gly Val Arg  Pro Ser Val
    1085                1090                1095

Asp Ser  Thr Arg Ser Ser Ile  Gln Leu Gly Gln Gln  Leu Pro Glu
    1100                1105                1110

Leu Asp  Thr Gly Glu Gly Phe  Ser Ile Pro Tyr Leu  Ser Ala Glu
    1115                1120                1125

Ala Thr  Ser Asp Leu Ser Tyr  Leu Ser Ser Pro Gly  Lys His Glu
    1130                1135                1140

Pro Ala  Pro His Pro Arg Ser  Gly Arg Asn Ser Ala  Ile Asp Ser
    1145                1150                1155

Gln Thr  Ser Ser Val Phe Tyr  Glu Gln Ser Gln Tyr  Gly Ser Thr
    1160                1165                1170

Leu Val  Asn Ser Asp Arg Gly  Ser Gly Glu Tyr Val  Ser His His
    1175                1180                1185

Ser Glu  Thr Pro Leu Ser Met  Met Asp Leu Thr Ser  Met Glu Thr
    1190                1195                1200

Met Asp  Arg Tyr Tyr Asp Gly  Arg Thr Gln Val Asp  Ser Asp Ala
```

```
    1205                1210                1215

Lys Ser  Phe Ile Gln Glu Ser  Glu Gly Leu Ser Ser  Glu Glu Arg
    1220                1225                1230

His Arg  Leu Ile Gln Arg Arg  Asn Val Ile Lys Glu  Leu Val Asp
    1235                1240                1245

Thr Glu  Ala Ile Phe Val Arg  Asp Met Asn Ile Val  Glu Glu Ile
    1250                1255                1260

Tyr Lys  Gly Thr Ala Glu Ala  Cys Pro Lys Leu Asp  Thr Lys Ile
    1265                1270                1275

Val Lys  Leu Ile Phe Arg Asn  Ser Asp Glu Ile Ile  Glu Phe His
    1280                1285                1290

Thr Ser  Phe Leu Val Leu Leu  Lys Glu Ala Val Ala  Ser Ile Tyr
    1295                1300                1305

Val Pro  Lys Gly Gly Arg Ser  Leu Val Ala Arg Glu  Asp Ser Ile
    1310                1315                1320

Tyr Ser  Glu Gln Gly Gln Thr  Ser Ile Val Asp Leu  Ser Asp Ala
    1325                1330                1335

Lys Asp  Arg Glu Thr Ser Leu  Gly Pro Thr Phe Gln  Ala Asn Met
    1340                1345                1350

Glu Lys  Met Lys Leu Ala His  Glu Gly Phe Leu Arg  Asn Ser Asp
    1355                1360                1365

Gln Ala  Ala Lys Lys Leu Ile  Gln Ile Gln Gln Asp  Pro Thr Val
    1370                1375                1380

Gln Ile  Trp Leu Asn Glu Cys  Asn Glu Val Ala Lys  Asp Leu Thr
    1385                1390                1395

Ala Ala  Trp Asp Leu Asp Ser  Leu Leu Ile Lys Pro  Met Gln Arg
    1400                1405                1410

Ile Thr  Lys Tyr Pro Asn Leu  Ile Met Thr Leu Leu  Gln His Thr
    1415                1420                1425

Pro Gln  Asp His Pro Asp Arg  Glu Ala Leu Val Met  Ala Lys Glu
    1430                1435                1440

Ala Leu  Glu Glu Ala Ile Ile  Glu Ile Asn Lys Thr  Lys Lys Asn
    1445                1450                1455

Phe Glu  Leu Val Gly Gln Ile  Val Gly Arg Lys Arg  Lys Glu Ser
    1460                1465                1470

Asp Val  Lys Ala Gly Leu Ala  Arg Ala Phe Gly Lys  Lys Val Asp
    1475                1480                1485

Lys Leu  Gln Gly Gly Thr Arg  Pro Pro Glu Asp Pro  Glu Tyr Leu
    1490                1495                1500

Lys Leu  Glu Glu Arg Phe Ser  Asp Asp Tyr Leu Arg  Leu Gln Val
    1505                1510                1515

Val Leu  Arg Asp Val Glu Phe  Tyr Thr Arg Gln Val  Ser Ser Tyr
    1520                1525                1530

Val His  Glu Phe Leu Gln Tyr  Leu Ser Ala Ile Glu  Leu Val Met
    1535                1540                1545

Arg Leu  Gln Pro Gly Ser Phe  Pro Glu Leu Glu Ser  Lys Trp Val
    1550                1555                1560

Arg Phe  Asn Ile Ser Ile Arg  Asp Ile Glu Lys Val  Ala Leu Glu
    1565                1570                1575

Gln His  Leu Ser Gln Ile Arg  Lys His Val Ile Glu  Pro Phe Glu
    1580                1585                1590

Gln Val  Ile Lys Ser Tyr Gly  Asn Pro Ser Leu Ala  Met Lys Lys
    1595                1600                1605
```

```
Arg Gln  Lys Arg Arg Val Val  Trp Glu Arg Ala Glu  Gln Leu Lys
    1610                 1615                 1620

Lys Ala  Gly Lys Ser Val Asp  Pro Lys Leu Lys Glu  Leu Val Glu
    1625                 1630                 1635

Gln Tyr  Glu Ala Leu Asn Asp  Thr Leu Ile Lys Glu  Leu Pro Lys
    1640                 1645                 1650

Leu Ser  Ala Leu Thr Glu Lys  Val Gly Asn Ile Cys  Leu Ser Asn
    1655                 1660                 1665

Leu Ile  Asn Ile Gln Ala Asn  Trp Tyr Phe Ile Trp  Arg Glu Lys
    1670                 1675                 1680

Met Arg  Ala Val Leu Pro Asp  Ser Pro Thr Met Pro  Asp Ile Glu
    1685                 1690                 1695

Glu Ile  Val Ser Thr Phe Gln  Arg Asp Phe Pro Tyr  Ala Asn Glu
    1700                 1705                 1710

Met Met  Ala Ser Ile Gly Ile  Ile Asn Pro Ala Tyr  Arg Gly Arg
    1715                 1720                 1725

Thr Ser  Gln Ser Thr Asn His  Gly Asp Asp Ala Gly  Leu Pro Arg
    1730                 1735                 1740

Thr Arg  Gly Arg Thr Ser Glu  Ser Val Asp Arg Gly  Trp Ser Gln
    1745                 1750                 1755

Ser Phe  Asn Gly Glu Gly Ala  Pro Ser Leu Pro Pro  Pro Asp Phe
    1760                 1765                 1770

Gly Lys  Arg His Ser Gly Ser  Phe Thr Leu Ser Pro  Ile Ser Ala
    1775                 1780                 1785

Gly Pro  Ser Ser Ser Gly Phe  Gly Thr Ser Ala Pro  Ser Pro His
    1790                 1795                 1800

Gln Tyr  Tyr Tyr Arg Asp Phe  Tyr Ala Gly Leu Ser  Ser Asn Gln
    1805                 1810                 1815

Ala Gly  Met Thr Ser Pro Arg  Ser Ala Glu Val Pro  Ala Thr Ser
    1820                 1825                 1830

Arg Ser  Leu Gly Gly Thr Arg  Pro Ser Thr Gly Lys  Ser Tyr Asp
    1835                 1840                 1845

Ser Ser  Ala Ile Ser Met Pro  Arg Gln Ser Thr Glu  Ser Ala Pro
    1850                 1855                 1860

His Ile  Arg Arg Asp Ser Gly  Thr Ala Tyr Tyr Ser  Ser Tyr His
    1865                 1870                 1875

Gln His  Asp Ser Arg Arg Phe  Ser Asn Leu Phe His  Ser Ala Leu
    1880                 1885                 1890

Pro Leu  Pro Asp Gly Pro Glu  Glu Ser Gln Arg Ser  Ser Arg Ala
    1895                 1900                 1905

Ser Ser  Arg Glu Arg Ala His  Ala Ser Asp Gly Tyr  Asn Ile Leu
    1910                 1915                 1920

Trp Leu  Ala Ala Ser Leu Phe  Glu Phe Asn Ile Ser  Thr Thr Lys
    1925                 1930                 1935

His Glu  Ala Gly Tyr Pro Tyr  Leu Thr Tyr Gln Ala  Gly Glu Ile
    1940                 1945                 1950

Phe Asp  Val Ile Ala Glu Lys  Gly Glu Leu Trp Leu  Ala Lys Asn
    1955                 1960                 1965

Gln Asp  Asp Pro Thr Asp Gln  Val Gly Trp Ile Trp  Ser Lys His
    1970                 1975                 1980

Phe Ala  Lys Leu Ala Asp Ser
    1985                 1990
```

<210> SEQ ID NO 3
<211> LENGTH: 5973
<212> TYPE: DNA
<213> ORGANISM: Hypocrea jecorina

<400> SEQUENCE: 3

```
atggacccgg acccggacct gcacctgcca gcacgagtag agcgcgcgag cctggatggt     60
agcgtgtttg tagcccacga tgcgcatccg ccggctcgcc atctgcccca tctccatctc    120
ccccagctgg cccatccagc ctcaaactca acctccaact tcaccttgcg ctcgcactcg    180
cactcgcccg ctgccggcga cgtcgtcctg cccgcctcaa ccgccaatgc ccacgtcctc    240
gcccaccatg cagctgccac cctagatcct gacgactact acaggagcta cgagacagcc    300
tccagccccg gcggcgagcc acaatcgctc ccaatggcct cgccagtccc gcctcccacg    360
ccggatgggg ctgctgcaag acacctgcag ccgcctgcaa atcgcagtgc tggccgtcag    420
ggtaccagta ataccgccgt gcgctccgcc tcgagccccc tcgaccgcag gccagccgcg    480
gcggcgccgt cgtcaagatc cccctcggcc agcgccccca gcgtgaggga tctgaagaag    540
cgcttcgatc agaacagcgg ccccaactcc atcccaagag ctcctccacg ccaggctgca    600
ccggtggccc gggtcagcaa gcaagagtcc agcaaaccca agcccaagcc caagcccagc    660
ctgtcggccc cttcgtccac gcacccaggc tctcgctcgg cggtccccgc ttccaactcg    720
tccaagcaat ctcggtcgtc gtcgtcgtcc aactcagcct cgacctcgcg ctcgacgtcg    780
acgccggccc cgtcagcccg ctcgcagaag ccacggcacg ttgagcgcga gcaggcggcg    840
ggaagttcgc ggtcgtttgc aaaccgtatt gggaaccatc agcctgagac atccactact    900
aacgggaact cgaacgcctc cagctctatg acaccacgcc cacacaagtc cccaccctca    960
gcctcccagc cgtcgccgcc atccccaaag tctaatcctc agttcccggg cctcctgttt   1020
ggcgaaatcc ccccgggcca gctcgacgtt gccgcgccag gctttggcat cgacaacatc   1080
cgcccgcgac gaacgtccga atccaacgtg cacggcctcg cggggcgtca acgcagcctc   1140
tccgacctcg aagccgagcc cgcgtccccg tccagctggt acagggacgt ccacatgtcc   1200
cgagggagca cgccgaaaac ccacgcgcga tctcgcagcg atctctcggc gctgaagccc   1260
atcctcacaa ccttgcatcc caagtcgcct acgcccgcat cggcgtcggc atcagcaaag   1320
acaagggcga aatcaccaac agtagctgct ttcgcggcag ccacggtaac ggcaacggct   1380
gtcgcagcag gggccgcggc cgccacccct tcggtctcgc acgcgtcggc agccgccagc   1440
tccaaactcc ccgtttccat cagcaggagg cttgcgagcc caaccaactc cagtcctacc   1500
tcttcgcgat cagcctcgcc ctctgcgctt cgcagactgc cagccaatgg tcgtagcaat   1560
agcagacagg ccaaaccgat cgcccccacg aaccgagcga aaacacccac gcagacgggt   1620
cgaaagcagc ctccccaggg gctcgttaca ccgagtaata gcaacaaccg gctccaagcg   1680
tacgtgtcca ccgcaccacc caagctctca ccgccattga ggagctctcg accgcgacag   1740
ccagtctccg tagcgacgac agcaagctcc cggatgaaag aggcggcggc caaggcgaag   1800
ccccctgcac ggccaaatgc acgggacggc ccttcgtcgt ccaagacgta cgatccggcg   1860
aagcgtaaaa tcatagtggg acccatagac ttcgagcagc gtcgggaaca cattcgactg   1920
gcatacacca agaccattcg cgaaagccag gcctttgagg tgcgccagaa agcggtggag   1980
aggaggcgga agcagatgga ggaggccaaa tcggaagccg cagccaccga agctacagcg   2040
acaagtagca cagctacagg cccatctacg tctgcggatt caccgaccac ggtgactgct   2100
ggagatgacg aggcgacgaa taaggggccc tcggacggcc atgcacgagt aattccagaa   2160
```

```
gtaatagcgg cagagacagg gctggtcgcg agcccctcgg cacaggagcc ggctgtggaa   2220
ctcccagctg atcatggctc tcgcgctgct gtggagaacc agggaaccct tctagaaatc   2280
ccgacagatg cagcctcgca cccggcatct ggcaagggtg atgattcgcc gacgctgggc   2340
atccccgggg gcttcccaga accctcaccg tcctccgccg cggccagaac gcagcggcct   2400
ctgtcgacca tttcaatcat ttcagccacg tctgctgtta cggagtttga tacagagccc   2460
caggcggagc tcgccgacct ggctatgtcc gatcggccgc tcagcccccca gatcatagtg   2520
ccgacgaggg agcgctctca gtatagaagc ccctttgagg acgacgattt cccatcgtcg   2580
ccgcctcggc cgcgtcctgc ggcccatccc catcaaatca gccaagatcg ccaccatatc   2640
gaccagccgt tcatccctga cgcttattac gacaatgagc atcgggagca ccccttggag   2700
acccatgccc agcaagatta ccaaaccatt gtgacgattc tgccgcagcc ctcacgcgag   2760
ccccctgctg ccgaggagac tgcgcaggcg gcatcttttc cccgactaga cattcaagat   2820
gaatctgact gccactcgga tctagaaagc gttccggcaa tggctcgtcg catgcgtagt   2880
gatgtcgacg atgccgccac tgatgcctgc accgaagaga cggacgaccg cgatgggatg   2940
gaggacgagc ggtccccgta ccgctatggc ggcaccctct cgtcgaacag ggcctctaca   3000
tgcgcatcat cggacataga aacgtttgac gaccttttgt acccttcgca tgacgagcag   3060
ctggatgcgg gcccaccaaa cagactactg gcgccgccct cgatctctcg ggccgacaga   3120
tcgagccacc agaccgcatg gacgaatgtc tccgtcgaaa gcattacgcg ctccgaggct   3180
tcagactctc ctgttctacg agccagctcc tggaagatgt ccggttcgtc cgggcgagac   3240
gactcttccc tcagaagcct cccctatagc ggagtcggcg tccgcccttc agtcgactcg   3300
acgcggtcgt cgattcagct tggccagcag ctcccggagc tagacacggg cgaaggcttc   3360
tccatcccgt atctgtccgc agaggcaacc tccgacctct cctacctctc ttcccccggg   3420
aaacacgagc cagcacctca cccgcgctct ggacggaact cggccatcga ctcgcaaacg   3480
tcgagcgtgt tctatgagca gtcccagtat ggcagcacgt tggtcaactc cgatcgcggg   3540
agtggagaat atgtctccca ccattcggaa actcctctgt cgatgatgga cttgacctcg   3600
atggagacta tggatcggta ctatgacggt cgcacccagg tggatagcga tgccaagtca   3660
ttcatccaag aatccgaggg gctaagcagc gaagagcggc atcgccttat ccagaggcgt   3720
aacgtcatca aggagcttgt ggataccgaa gcaatttttg taagagacat gaacattgtg   3780
gaggaaatct acaagggcac cgcagaggcg tgccccaagc tggacaccaa gattgtcaag   3840
ctcatcttca ggaacagcga cgagattatc gagtttcaca cctcgttcct cgtcctcctc   3900
aaagaggcag tggccagcat ttacgtaccg aagggcggcc ggtctctcgt cgcgagagaa   3960
gactccatct attcggaaca aggccagact tccatcgtcg acctcagcga tgccaaggac   4020
agagagacgt cgctcggtcc aactttccaa gccaacatgg agaagatgaa gcttgctcac   4080
gaagggttcc tgcgaaacag cgaccaagca gcaaagaaac tgatccagat ccagcaggac   4140
ccgacggtgc agatatggct gaacgagtgt aatgaggtag ccaaggacct gacagctgcc   4200
tgggatctgg actcccttct catcaagccg atgcaacgaa tcacaaagta tccgaatctg   4260
atcatgacgc tccttcagca cacgccccag gaccaccccg atcgggaggc cctcgtgatg   4320
gccaaagagg cgctcgaaga ggccattatc gagatcaaca agacgaagaa gaactttgag   4380
ctggtcggac agatcgtcgg tagaaaacgt aaggagtccg acgtgaaggc cggactcgct   4440
cgtgcctttg gcaagaaggt ggacaagctg caaggcggaa ctcggccacc ggaggatcca   4500
```

```
gaatatctca agctggagga aaggttcagc gacgattact tgcggctaca ggtcgtcttg   4560

cgcgatgtcg agttctacac ccggcaagtc tcatcgtatg tgcacgagtt cctgcagtac   4620

ctatcagcca tcgagctggt catgcgtctt cagccgggca gcttccccga gctggagagc   4680

aagtgggtgc gcttcaatat ctccattcgc gacattgaga aggtagcgct cgagcagcat   4740

ctgtcacaga ttcgaaagca tgtcattgag ccttttgagc aggtcatcaa gtcctacggg   4800

aacccctcgc tggctatgaa gaagagacaa aagcgccgag tcgtgtggga gcgcgcagag   4860

cagctgaaga aggcaggcaa aagcgtcgat cccaagctta aggagctggt tgagcagtat   4920

gaagctctca acgatacgct aatcaaggag cttcccaagc tttcggcgct gacggagaag   4980

gtgggaaaca tttgtctcag caatctcatc aacatccagg ccaattggta cttcatttgg   5040

agggagaaga tgagagctgt gctgccggac tcgcccacga tgccagacat tgaggaaata   5100

gtctcgactt tccagcgaga ctttccctat gcgaacgaga tgatggccag catcggcatc   5160

atcaacccag cctaccgcgg aaggacatca caatcaacga accacggaga cgacgccggc   5220

ctgcccagga ctagaggccg aacctcagag tcggtagata ggggatggag tcagtctttc   5280

aacggcgaag gcgcaccaag cctaccgcct cccgattttg gcaaacggca tagcggctcg   5340

tttaccctct cccccatcag cgccggcccg tcctcctctg gcttcgggac gtcagctccc   5400

agtccccacc agtactatta tcgtgacttt tatgccggcc tgtcaagcaa ccaggcggga   5460

atgacatccc cgagatcggc cgaggtacca gcaacctctc gatcgctcgg aggcacgcgg   5520

ccgagtacgg gcaaaagcta cgattcgtcg gcaatctcaa tgccgagaca gagcacggag   5580

tcggcgcctc acatccgacg ggactcgggc acggcgtact attccagcta ccaccagcac   5640

gacagccgta gattctcaaa tctctttcac tctgcccttc ctctaccgga cggccccgaa   5700

gagagtcagc ggtcctctag agcatcatcg cgggagcgag cacatgcttc tgatgggtac   5760

aatatcctat ggctggcagc gtcgctcttc gagtttaaca tctcgacaac caagcacgag   5820

gctggctatc cttatctgac gtatcaggcc ggcgagatat tcgatgtaat tgccgagaaa   5880

ggcgagcttt ggcttgccaa gaatcaagac gacccaacgg accaggtggg ctggatctgg   5940

tccaaacact ttgcgaaatt ggccgactca tag                                5973
```

<210> SEQ ID NO 4
<211> LENGTH: 1244
<212> TYPE: PRT
<213> ORGANISM: Hypocrea jecorina

<400> SEQUENCE: 4

```
Met Asp Pro Asp Pro Asp Leu His Leu Pro Ala Arg Val Glu Arg Ala
1               5                   10                  15

Ser Leu Asp Gly Ser Val Phe Val Ala His Asp Ala His Pro Pro Ala
            20                  25                  30

Arg His Leu Pro His Leu His Leu Pro Gln Leu Ala His Pro Ala Ser
        35                  40                  45

Asn Ser Thr Ser Asn Phe Thr Leu Arg Ser His Ser His Ser Pro Ala
    50                  55                  60

Ala Gly Asp Val Val Leu Pro Ala Ser Thr Ala Asn Ala His Val Leu
65                  70                  75                  80

Ala His His Ala Ala Ala Thr Leu Asp Pro Asp Asp Tyr Tyr Arg Ser
                85                  90                  95

Tyr Glu Thr Ala Ser Ser Pro Gly Gly Glu Pro Gln Ser Leu Pro Met
            100                 105                 110
```

-continued

```
Ala Ser Pro Val Pro Pro Pro Thr Pro Asp Gly Ala Ala Ala Arg His
        115                 120                 125

Leu Gln Pro Pro Ala Asn Arg Ser Ala Gly Arg Gln Gly Thr Ser Asn
    130                 135                 140

Thr Ala Val Arg Ser Ala Ser Ser Pro Leu Asp Arg Arg Pro Ala Ala
145                 150                 155                 160

Ala Ala Pro Ser Ser Arg Ser Pro Ser Ala Ser Ala Pro Ser Val Arg
                165                 170                 175

Asp Leu Lys Lys Arg Phe Asp Gln Asn Ser Gly Pro Asn Ser Ile Pro
            180                 185                 190

Arg Ala Pro Pro Arg Gln Ala Ala Pro Val Ala Arg Val Ser Lys Gln
        195                 200                 205

Glu Ser Ser Lys Pro Lys Pro Lys Pro Lys Pro Ser Leu Ser Ala Pro
    210                 215                 220

Ser Ser Thr His Pro Gly Ser Arg Ser Ala Val Pro Ala Ser Asn Ser
225                 230                 235                 240

Ser Lys Gln Ser Arg Ser Ser Ser Ser Ser Asn Ser Ala Ser Thr Ser
                245                 250                 255

Arg Ser Thr Ser Thr Pro Ala Pro Ser Ala Arg Ser Gln Lys Pro Arg
            260                 265                 270

His Val Glu Arg Glu Gln Ala Ala Gly Ser Ser Arg Ser Phe Ala Asn
        275                 280                 285

Arg Ile Gly Asn His Gln Pro Glu Thr Ser Thr Thr Asn Gly Asn Ser
    290                 295                 300

Asn Ala Ser Ser Ser Met Thr Pro Arg Pro His Lys Ser Pro Pro Ser
305                 310                 315                 320

Ala Ser Gln Pro Ser Pro Pro Ser Pro Lys Ser Asn Pro Gln Phe Pro
                325                 330                 335

Gly Leu Leu Phe Gly Glu Ile Pro Pro Gly Gln Leu Asp Val Ala Ala
            340                 345                 350

Pro Gly Phe Gly Ile Asp Asn Ile Arg Pro Arg Arg Thr Ser Glu Ser
        355                 360                 365

Asn Val His Gly Leu Ala Gly Arg Gln Arg Ser Leu Ser Asp Leu Glu
    370                 375                 380

Ala Glu Pro Ala Ser Pro Ser Ser Trp Tyr Arg Asp Val His Met Ser
385                 390                 395                 400

Arg Gly Ser Thr Pro Lys Thr His Ala Arg Ser Arg Ser Asp Leu Ser
                405                 410                 415

Ala Leu Lys Pro Ile Leu Thr Thr Leu His Pro Lys Ser Pro Thr Pro
            420                 425                 430

Ala Ser Ala Ser Ala Ser Ala Lys Thr Arg Ala Lys Ser Pro Thr Val
        435                 440                 445

Ala Ala Phe Ala Ala Ala Thr Val Thr Ala Thr Ala Val Ala Ala Gly
    450                 455                 460

Ala Ala Ala Ala Thr Pro Ser Val Ser His Ala Ser Ala Ala Ala Ser
465                 470                 475                 480

Ser Lys Leu Pro Val Ser Ile Ser Arg Arg Leu Ala Ser Pro Thr Asn
                485                 490                 495

Ser Ser Pro Thr Ser Ser Arg Ser Ala Ser Pro Ser Ala Leu Arg Arg
            500                 505                 510

Leu Pro Ala Asn Gly Arg Ser Asn Ser Arg Gln Ala Lys Pro Ile Ala
        515                 520                 525

Pro Thr Asn Arg Ala Lys Thr Pro Thr Gln Thr Gly Arg Lys Gln Pro
```

```
    530                 535                 540

Pro Gln Gly Leu Val Thr Pro Ser Asn Ser Asn Asn Arg Leu Gln Ala
545                 550                 555                 560

Tyr Val Ser Thr Ala Pro Pro Lys Leu Ser Pro Pro Leu Arg Ser Ser
                565                 570                 575

Arg Pro Arg Gln Pro Val Ser Val Ala Thr Thr Ala Ser Ser Arg Met
            580                 585                 590

Lys Glu Ala Ala Ala Lys Ala Lys Pro Pro Ala Arg Pro Asn Ala Arg
        595                 600                 605

Asp Gly Pro Ser Ser Ser Lys Thr Tyr Asp Pro Ala Lys Arg Lys Ile
    610                 615                 620

Ile Val Gly Pro Ile Asp Phe Glu Gln Arg Arg Glu His Ile Arg Leu
625                 630                 635                 640

Ala Tyr Thr Lys Thr Ile Arg Glu Ser Gln Ala Phe Glu Val Arg Gln
                645                 650                 655

Lys Ala Val Glu Arg Arg Arg Lys Gln Met Glu Glu Ala Lys Ser Glu
            660                 665                 670

Ala Ala Ala Thr Glu Ala Thr Ala Thr Ser Ser Thr Ala Thr Gly Pro
        675                 680                 685

Ser Thr Ser Ala Asp Ser Pro Thr Thr Val Thr Ala Gly Asp Asp Glu
    690                 695                 700

Ala Thr Asn Lys Gly Pro Ser Asp Gly His Ala Arg Val Ile Pro Glu
705                 710                 715                 720

Val Ile Ala Ala Glu Thr Gly Leu Val Ala Ser Pro Ser Ala Gln Glu
                725                 730                 735

Pro Ala Val Glu Leu Pro Ala Asp His Gly Ser Arg Ala Ala Val Glu
            740                 745                 750

Asn Gln Gly Thr Leu Leu Glu Ile Pro Thr Asp Ala Ala Ser His Pro
        755                 760                 765

Ala Ser Gly Lys Gly Asp Asp Ser Pro Thr Leu Gly Ile Pro Gly Gly
    770                 775                 780

Phe Pro Glu Pro Ser Pro Ser Ser Ala Ala Ala Arg Thr Gln Arg Pro
785                 790                 795                 800

Leu Ser Thr Ile Ser Ile Ile Ser Ala Thr Ser Ala Val Thr Glu Phe
                805                 810                 815

Asp Thr Glu Pro Gln Ala Glu Leu Ala Asp Leu Ala Met Ser Asp Arg
            820                 825                 830

Pro Leu Ser Pro Gln Ile Ile Val Pro Thr Arg Glu Arg Ser Gln Tyr
        835                 840                 845

Arg Ser Pro Phe Glu Asp Asp Asp Phe Pro Ser Ser Pro Pro Arg Pro
    850                 855                 860

Arg Pro Ala Ala His Pro His Gln Ile Ser Gln Asp Arg His His Ile
865                 870                 875                 880

Asp Gln Pro Phe Ile Pro Asp Ala Tyr Tyr Asp Asn Glu His Arg Glu
                885                 890                 895

His Pro Leu Glu Thr His Ala Gln Gln Asp Tyr Gln Thr Ile Val Thr
            900                 905                 910

Ile Leu Pro Gln Pro Ser Arg Glu Pro Pro Ala Ala Glu Glu Thr Ala
        915                 920                 925

Gln Ala Ala Ser Phe Pro Arg Leu Asp Ile Gln Asp Glu Ser Asp Cys
    930                 935                 940

His Ser Asp Leu Glu Ser Val Pro Ala Met Ala Arg Arg Met Arg Ser
945                 950                 955                 960
```

```
Asp Val Asp Asp Ala Ala Thr Asp Ala Cys Thr Glu Glu Thr Asp Asp
                965                 970                 975

Arg Asp Gly Met Glu Asp Glu Arg Ser Pro Tyr Arg Tyr Gly Gly Thr
            980                 985                 990

Leu Ser Ser Asn Arg Ala Ser Thr  Cys Ala Ser Ser Asp  Ile Glu Thr
        995                 1000                 1005

Phe Asp  Asp Leu Leu Tyr Pro  Ser His Asp Glu Gln  Leu Asp Ala
    1010                 1015                 1020

Gly Pro  Pro Asn Arg Leu Leu  Ala Pro Pro Ser Ile  Ser Arg Ala
    1025                 1030                 1035

Asp Arg  Ser Ser His Gln Thr  Ala Trp Thr Asn Val  Ser Val Glu
    1040                 1045                 1050

Ser Ile  Thr Arg Ser Glu Ala  Ser Asp Ser Pro Val  Leu Arg Ala
    1055                 1060                 1065

Ser Ser  Trp Lys Met Ser Gly  Ser Ser Gly Arg Asp  Asp Ser Ser
    1070                 1075                 1080

Leu Arg  Ser Leu Pro Tyr Ser  Gly Val Gly Val Arg  Pro Ser Val
    1085                 1090                 1095

Asp Ser  Thr Arg Ser Ser Ile  Gln Leu Gly Gln Gln  Leu Pro Glu
    1100                 1105                 1110

Leu Asp  Thr Gly Glu Gly Phe  Ser Ile Pro Tyr Leu  Ser Ala Glu
    1115                 1120                 1125

Ala Thr  Ser Asp Leu Ser Tyr  Leu Ser Ser Pro Gly  Lys His Glu
    1130                 1135                 1140

Pro Ala  Pro His Pro Arg Ser  Gly Arg Asn Ser Ala  Ile Asp Ser
    1145                 1150                 1155

Gln Thr  Ser Ser Val Phe Tyr  Glu Gln Ser Gln Tyr  Gly Ser Thr
    1160                 1165                 1170

Leu Val  Asn Ser Asp Arg Gly  Ser Gly Glu Tyr Val  Ser His His
    1175                 1180                 1185

Ser Glu  Thr Pro Leu Ser Met  Met Asp Leu Thr Ser  Met Glu Thr
    1190                 1195                 1200

Met Asp  Arg Tyr Tyr Asp Gly  Arg Thr Gln Val Asp  Ser Asp Ala
    1205                 1210                 1215

Lys Ser  Phe Ile Gln Glu Ser  Glu Gly Leu Ser Ser  Glu Glu Arg
    1220                 1225                 1230

His Arg  Leu Ile Gln Arg Arg  Asn Val Ile Lys
    1235                 1240


<210> SEQ ID NO 5
<211> LENGTH: 213
<212> TYPE: PRT
<213> ORGANISM: Hypocrea jecorina

<400> SEQUENCE: 5

Val Ile Glu Glu Leu Val Asp Thr Glu Ala Ile Phe Val Arg Asp Met
1               5                   10                  15

Asn Ile Val Glu Glu Ile Tyr Lys Gly Thr Ala Glu Ala Cys Pro Lys
            20                  25                  30

Leu Asp Thr Lys Ile Val Lys Leu Ile Phe Arg Asn Ser Asp Glu Ile
        35                  40                  45

Ile Glu Phe His Thr Ser Phe Leu Val Leu Leu Lys Glu Ala Val Ala
    50                  55                  60

Ser Ile Tyr Val Pro Lys Gly Gly Arg Ser Leu Val Ala Arg Glu Asp
```

```
65                  70                  75                  80

Ser Ile Tyr Ser Glu Gln Gly Gln Thr Ser Ile Val Asp Leu Ser Asp
                85                  90                  95

Ala Lys Asp Arg Glu Thr Ser Leu Gly Pro Thr Phe Gln Ala Asn Met
            100                 105                 110

Glu Lys Met Lys Leu Ala His Glu Gly Phe Leu Arg Asn Ser Asp Gln
        115                 120                 125

Ala Ala Lys Lys Leu Ile Gln Ile Gln Gln Asp Pro Thr Val Gln Ile
    130                 135                 140

Trp Leu Asn Glu Cys Asn Glu Val Ala Lys Asp Leu Thr Ala Ala Trp
145                 150                 155                 160

Asp Leu Asp Ser Leu Leu Ile Lys Pro Met Gln Arg Ile Thr Lys Tyr
                165                 170                 175

Pro Asn Leu Ile Met Thr Leu Leu Gln His Thr Pro Gln Asp His Pro
            180                 185                 190

Asp Arg Glu Ala Leu Val Met Ala Lys Glu Ala Leu Glu Glu Ala Ile
        195                 200                 205

Ile Glu Ile Asn Lys
    210


<210> SEQ ID NO 6
<211> LENGTH: 102
<212> TYPE: PRT
<213> ORGANISM: Hypocrea jecorina

<400> SEQUENCE: 6

Ala Leu Glu Gln His Leu Ser Gln Ile Arg Lys His Val Ile Glu Pro
1               5                   10                  15

Phe Glu Gln Val Ile Lys Ser Tyr Gly Asn Pro Ser Leu Ala Met Lys
            20                  25                  30

Lys Arg Gln Lys Arg Arg Val Val Trp Glu Arg Ala Glu Gln Leu Lys
        35                  40                  45

Lys Ala Gly Lys Ser Val Asp Pro Lys Leu Lys Glu Leu Val Glu Gln
    50                  55                  60

Tyr Glu Ala Leu Asn Asp Thr Leu Ile Lys Glu Leu Pro Lys Leu Ser
65                  70                  75                  80

Ala Leu Thr Glu Lys Val Gly Asn Ile Cys Leu Ser Asn Leu Ile Asn
                85                  90                  95

Ile Gln Ala Asn Trp Tyr
            100


<210> SEQ ID NO 7
<211> LENGTH: 72
<212> TYPE: PRT
<213> ORGANISM: Hypocrea jecorina

<400> SEQUENCE: 7

Gly Tyr Asn Ile Leu Trp Leu Ala Ala Ser Leu Phe Glu Phe Asn Ile
1               5                   10                  15

Ser Thr Thr Lys His Glu Ala Gly Tyr Pro Tyr Leu Thr Tyr Gln Ala
            20                  25                  30

Gly Glu Ile Phe Asp Val Ile Ala Glu Lys Gly Glu Leu Trp Leu Ala
        35                  40                  45

Lys Asn Gln Asp Asp Pro Thr Asp Gln Val Gly Trp Ile Trp Ser Lys
    50                  55                  60

His Phe Ala Lys Leu Ala Asp Ser
```

65 70

<210> SEQ ID NO 8
<211> LENGTH: 20
<212> TYPE: RNA
<213> ORGANISM: Artificial Sequence
<220> FEATURE:
<223> OTHER INFORMATION: synthetic

<400> SEQUENCE: 8
cauucaucca agaauccgag 20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
cctaactaac gtctgacatc g 21

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
cgtaccattt gactgatacg atg 23

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
gagctagaca cgggcgaag 19

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
aggaaccctt cgtgagcaag 20

<210> SEQ ID NO 13
<211> LENGTH: 20
<212> TYPE: RNA
<213> ORGANISM: Artificial Sequence
<220> FEATURE:
<223> OTHER INFORMATION: synthetic

<400> SEQUENCE: 13
auuguggagg aaaucuacaa 20

<210> SEQ ID NO 14
<211> LENGTH: 1026
<212> TYPE: DNA
<213> ORGANISM: Artificial Sequence
<220> FEATURE:
<223> OTHER INFORMATION: synthetic

<400> SEQUENCE: 14
atgaaaaagc ctgaactcac cgcgacgtct gtcgagaagt ttctgatcga aaagttcgac 60
agcgtctccg acctgatgca gctctcggag ggcgaagaat ctcgtgcttt cagcttcgat 120
gtaggagggc gtggatatgt cctgcgggta aatagctgcg ccgatggttt ctacaaagat 180
cgttatgttt atcggcactt tgcatcggcc gcgctcccga ttccggaagt gcttgacatt 240
ggggaattca gcgagagcct gacctattgc atctcccgcc gtgcacaggg tgtcacgttg 300
caagacctgc ctgaaaccga actgcccgct gttctgcagc cggtcgcgga ggccatggat 360
gcgatcgctg cggccgatct tagccagacg agcgggttcg gcccattcgg accgcaagga 420
atcggtcaat acactacatg gcgtgatttc atatgcgcga ttgctgatcc ccatgtgtat 480
cactggcaaa ctgtgatgga cgacaccgtc agtgcgtccg tcgcgcaggc tctcgatgag 540
ctgatgcttt gggccgagga ctgccccgaa gtccggcacc tcgtgcacgc ggatttcggc 600
tccaacaatg tcctgacgga caatggccgc ataacagcgg tcattgactg gagcgaggcg 660
atgttcgggg attcccaata cgaggtcgcc aacatcttct tctggaggcc gtggttggct 720
tgtatggagc agcagacgcg ctacttcgag cggaggcatc cggagcttgc aggatcgccg 780
cgcctccggg cgtatatgct ccgcattggt cttgaccaac tctatcagag cttggttgac 840
ggcaatttcg atgatgcagc ttgggcgcag ggtcgatgcg acgcaatcgt ccgatccgga 900
gccgggactg tcgggcgtac acaaatcgcc cgcagaagcg cggccgtctg gaccgatggc 960
tgtgtagaag tactcgccga tagtggaaac cgacgcccca gcactcgtcc gagggcaaag 1020
gaatag 1026

<210> SEQ ID NO 15
<211> LENGTH: 801
<212> TYPE: DNA
<213> ORGANISM: Artificial Sequence
<220> FEATURE:
<223> OTHER INFORMATION: synthetic

<400> SEQUENCE: 15
catcagcgtt ggctttccgt ctccattggc tcttggcaat tcggtcagcg gggctgactg 60
cctcaggtgg ggcagtgcta gtgtgtgtac cgacccgcag gattggtgct ttgcccagag 120
ctctacagaa tagcgcgcgc atccatatgt tagttctgca attttcttgt atcggtgctg 180
tgactcatac ttcccccttt ggctggcctt gcggcaacca ataagaacgc acagtgaaat 240
cttgcgggtg gggagtggat ccatggcgcc tgcattggct tggggacgcg cactgtcgca 300
cacttccatc tgacctttca gaagggtttc gtggtgggca aggaccaacc ggttgcgcgg 360
ccgtgcgtgg gtgcctcgcc cggcactgcc agggccactg cagtggcagt ttgctgcctg 420
atacaaaatc cttccctccg cccagttttc cctctttgac cttcctttct tcttctctgc 480
aaccaaatcc accctatcaa accaaaacag tatctcgacc gaggtatcaa cctgaatcag 540
caacatcgta gccagcattt gtctccgtct ctgcagaacc agcgagttgc aaacattatc 600
caggcaacag ggcaccaact cacttcttcg gctttcacca atcggtacag ctcttctcag 660
aactcgcgtc cgcaacagtt ctacgcttcc tcagcacctt cttcagcttc aatcctgaac 720
actcagaacc gcgcacagca gcgccctcct gttcccttgt ttcccaaaag taccggtagt 780
atttcgcacg gaaagcaggg c 801

<210> SEQ ID NO 16
<211> LENGTH: 741
<212> TYPE: DNA
<213> ORGANISM: Artificial Sequence
<220> FEATURE:
<223> OTHER INFORMATION: synthetic

<400> SEQUENCE: 16
agtagatgcc gaccgggatc cacttaacgt tactgaaatc atcaaacagc ttgacgaatc 60
tggatataag atcgttggtg tcgatgtcag ctccggagtt gagacaaatg gtgttcagga 120
tctcgataag atacgttcat ttgtccaagc agcaaagagt gccttctagt gatttaatag 180
ctccatgtca acaagaataa aacgcgtttc gggtttacct cttccagata cagctcatct 240
gcaatgcatt aatgcattgg acctcgcaac cctagtacgc ccttcaggct ccggcgaagc 300
agaagaatag cttagcagag tctattttca ttttcgggag acgagatcaa gcagatcaac 360
ggtcgtcaag agacctacga gactgaggaa tccgctcttg gctccacgcg actatatatt 420
tgtctctaat tgtactttga catgctcctc ttctttactc tgatagcttg actatgaaaa 480
ttccgtcacc agcccctggg ttcgcaaaga taattgcact gtttcttcct tgaactctca 540
agcctacagg acacacattc atcgtaggta taaacctcga aaatcattcc tactaagatg 600
ggtatacaat agtaaccatg gttgcctagt gaatgctccg taacacccaa tacgccggcc 660
gaaacttttt tacaactctc ctatgagtcg tttacccaga atgcacaggt acacttgttt 720
agaggtaatc cttctttcta g 741

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
tggctttccg tctccattg 19

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
agtgtacctg tgcattctgg g 21

<210> SEQ ID NO 19
<211> LENGTH: 1957
<212> TYPE: DNA
<213> ORGANISM: Artificial Sequence
<220> FEATURE:
<223> OTHER INFORMATION: synthetic

<400> SEQUENCE: 19
attaaggagg ggacgataca cgcaccatgg accccagtgg ggaagcaaga gcgggaagga 60
gagctgcgag acgtacagtg tgaattgctt cacgtctaaa gtatcaaggt atggagctgg 120
atggatgggc taaggtagta gacggcttcc ctcagcaact gagcttagtt atgatgctat 180
aacgtccact ttgatctgcg aaattgggca aaaaaaaaaa aaaaaaaaaa aaaaaaaaaa 240
aaaaaaaaaa gaatctattg cattaatgga catatataaa ggtcaaaagg ccgcagaatt 300

-continued

```
gacgtcgtag tctagccagg tagttgatgc cggatctatg ctcttcaccg ttcagagacg    360
aaacttttac ttcattaggg ggagtccaac ttttcattct cactctgtga gaagctgtgt    420
cacaatactt cagaggcatt aaagctacct cagctcttta aacatgtcaa ttctatcaaa    480
attaggtatg tgattcaagt agtgaacaat atgtggccgt tactcgagtt tataggtgac    540
aacatgctct caaagcgctc atggctggca caagcctgga aagaaccaac acaaagcata    600
ctgcagcaaa tcagctgaat tcgtcaccaa ttaagtgaac atcaacctga aggcagagta    660
tgaggccaga agcacatctg gatcgcagat catggattgc cctcttgtt  gaagatgaga    720
atctagaaag atggcggggt atgagataag agcgatgggg gggcacatca tcttccaaga    780
caaacaacct ttgcagagtc aggcaatttt tcgtataaga gcaggaggag ggagtccagt    840
catttcatca gcggtaaaat cactctagac aatcttcaag atgagttctg ccttgggtga    900
cttatagcca tcatcatacc tagacagaag cttgtgggat actaagacca acgtacaagc    960
tcgcactgta cgctttgact tccatgtgaa aactcgatac ggcgcgcctc taaattttat   1020
agctcaacca ctccaatcca acctctgcat ccctctcact cgtcctgatc tactgttcaa   1080
atcagagaat aaggacacta tccaaatcca acagaatggc taccacctcc cagctgcctg   1140
cctacaagca ggacttcctc aaatccgcca tcgacggcgg cgtcctcaag tttggcagct   1200
tcgagctcaa gtccaagcgg atatcccct  acttcttcaa cgcgggcgaa ttccacacgg   1260
cgcgcctcgc cggcgccatc gcctccgcct ttgcaaagac catcatcgag gcccaggaga   1320
aggccggcct agagttcgac atcgtcttcg gcccggccta caagggcatc ccgctgtgct   1380
ccgccatcac catcaagctc ggcgagctgg cgccccagaa cctggaccgc gtctcctact   1440
cgtttgaccg caaggaggcc aaggaccacg gcgagggcgg caacatcgtc ggcgcttcgc   1500
tcaagggcaa gagggtcctg attgtcgacg acgtcatcac cgccggcacc gccaagaggg   1560
acgccattga gaagatcacc aaggagggcg gcatcgtcgc cggcatcgtc gtggccctgg   1620
accgcatgga gaagctcccc gctgcggatg gcgacgactc caagcctgga ccgagtgcca   1680
ttggcgagct gaggaaggag tacggcatcc ccatctttgc catcctcact ctggatgaca   1740
ttatcgatgg catgaagggc tttgctaccc ctgaggatat caagaacacg gaggattacc   1800
gtgccaagta caaggcgact gactgattga ggcgttcaat gtcagaaggg agagtaagac   1860
tgaaaaggtg gaaagaagag gcaaattgtt gttattatta ttattctatc tcgaatcttc   1920
tagatcttgt cgtaaataaa caagcgtaac tagctag                            1957
```

FUNGAL STRAINS COMPRISING ENHANCED PROTEIN PRODUCTIVITY PHENOTYPES AND METHODS THEREOF

TECHNICAL FIELD

The present disclosure is generally related to the fields of biology, molecular biology, filamentous fungi, yeast, fermentation, genetics, industrial protein production and the like. More particularly, the present strains and methods of the disclosure relate to genetic modifications in filamentous fungi that give rise to variant (modified) strains having altered phenotypes, wherein such modified strains are particularly well-suited for growth in submerged cultures (e.g., large-scale production of proteins for industrial/commercial applications).

CROSS REFERENCE TO RELATED APPLICATIONS

This application claims benefit to U.S. Provisional Patent Application No. 62/932,525, filed Nov. 8, 2019, which is incorporated herein by referenced in its entirety.

REFERENCE TO A SEQUENCE LISTING

The contents of the electronic submission of the text file Sequence Listing, named "NB41383-WO-PCT_Sequence-Listing.txt" was created on Oct. 27, 2020 and is 55 KB in size, which is hereby incorporated by reference in its entirety.

BACKGROUND

Filamentous fungi (e.g., *Aspergillus* sp., *Penicillium* sp., *Talaromyces* sp., *Fusarium* sp., *Myceliophthora* sp., *Neurospora* sp., *Candida* sp., *Trichoderma* sp., and the like) are capable of expressing native and heterologous proteins to high levels, making them well-suited for the large-scale production of proteins (e.g., enzymes, antibodies, peptides, etc.) and/or metabolites for industrial and/or commercial applications such as pharmaceutical applications, animal health applications, food applications, beverage applications, laundry and textile applications, and the like. Filamentous fungi are typically grown in mycelial submerged cultures in bioreactors (fermentors), which bioreactors are adapted to introduce and distribute oxygen and nutrients into the culture medium (i.e., culture broth). For example, the filamentous fungus *Trichoderma reesei* (*T. reesei*; an anamorph of the fungus *Hypocrea jecorina*) is known to be an efficient producer of cellulase enzymes.

As such, filamentous fungi have been utilized for their ability to produce proteins (e.g., enzymes), which proteins are valuable in the production of commodities such as cellulosic (derived) ethanol, textile processing, grain processing, detergents, fibers/pulp/paper, food additives, feed additives and the like. For example, recombinant gene expression in such fungal host strains is a common method for the production of proteins (i.e., for industrial and commercial purposes) and as such, protein productivity improvements of a fungal host strain are an important economic factor of protein production costs. Thus, as appreciated by one of skill in the art, such novel compositions and methods for enhancing protein production in filamentous fungal strains are of significant commercial interest.

SUMMARY

The present disclosure is generally related to modified filamentous fungal strains (cells) comprising enhanced protein productivity phenotypes, wherein such modified strains are particularly well-suited for growth in submerged cultures (e.g., large-scale production of proteins for industrial/commercial applications). Thus, certain embodiments of the disclosure are related to such variant (modified) strains of filamentous fungus derived (obtained) from parental strains comprising a gene encoding a native GEF1 protein, wherein the variant strain comprises a genetic modification which disrupts or deletes the gene encoding the native GEF1 protein, wherein the variant strain comprises an increased protein productivity phenotype (i.e., relative to the parental strain) when grown/cultivated/fermented under the same conditions.

BRIEF DESCRIPTION OF THE BIOLOGICAL SEQUENCES

SEQ ID NO: 1 is a *T. reesei* polynucleotide sequence encoding a native GEF1 protein comprising SEQ ID NO: 2.

SEQ ID NO: 2 is the amino acid sequence of the native full length GEF1 protein encoded by the polynucleotide of SEQ ID NO: 1.

SEQ ID NO: 3 is an open reading frame (ORF) encoding the native full length GEF1 protein of SEQ ID NO: 2.

SEQ ID NO: 4 is a C-terminally truncated GEF1 variant protein comprising amino acid positions 1-1,244 of SEQ ID NO: 2.

SEQ ID NO: 5 is the amino acid sequence of the GEF1 domain present in SEQ ID NO: 2.

SEQ ID NO: 6 is the amino acid sequence of the BAR domain present in SEQ ID NO: 2.

SEQ ID NO: 7 is the amino acid sequence of a conserved, unknown domain present in SEQ ID NO: 2.

SEQ ID NO: 8 is a target site 3 (TS3) RNA sequence within the *T. reesei* GEF1 gene.

SEQ ID NO: 9 is the nucleic acid sequence of primer AL950.

SEQ ID NO: 10 is the nucleic acid sequence of primer AL952.

SEQ ID NO: 11 is the nucleic acid sequence of primer RhoF1.

SEQ ID NO: 12 is the nucleic acid sequence of primer RhoR1.

SEQ ID NO: 13 is a target site 4 (TS4) RNA sequence within the *T. reesei* GEF1 gene.

SEQ ID NO: 14 is the nucleic acid sequence of a hygromycin phosphotransferase marker gene.

SEQ ID NO: 15 is a *Neurospora crassa* cpcl promoter nucleic acid sequence.

SEQ ID NO: 16 is an *Aspergillus nidulans* trpC terminator nucleic acid sequence.

SEQ ID NO: 17 is the nucleic acid sequence of primer HygF1.

SEQ ID NO: 18 is the nucleic acid sequence of primer HygR1.

SEQ ID NO: 19 is the nucleic acid sequence of a pyr2 marker gene.

BRIEF DESCRIPTION OF THE DRAWINGS

FIG. 1 presents a polynucleotide sequence (SEQ ID NO: 1; FIG. 1A-FIG. 1B) encoding a native *Trichoderma* sp. GEF1 protein homologue comprising the amino acid sequence of SEQ ID NO: 2. As shown in FIG. 1A and FIG. 1B, the DNA sequence encoding the GEF1 protein (SEQ ID NO: 2) comprises two (2) introns, presented in lower case (nucleotide) letters and three (3) exons, presented in upper case (nucleotide) letters, wherein the Cas9 target site 3 (TS3) nucleotides are presented as double underlined upper case letters, the Cas9 target site 4 (TS4) nucleotides are presented as single underlined upper case letters and the bold upper case codon GAG of the wild-type sequence (SEQ ID NO: 1), which codon was mutated to a premature (TAG) stop codon in mutant strain, thereby encoding a C-terminally truncated GEF1 protein (FIG. 1B).

FIG. 2 shows the open reading frame (ORF) sequence (SEQ ID NO: 3; FIG. 2A-FIG. 2B) encoding the native GEF1 protein of SEQ ID NO: 2.

FIG. 3 shows the amino acid sequences of a native GEF1 protein (SEQ ID NO: 2; FIG. 3A) and a variant (C-terminally truncated) GEF1 protein (SEQ ID NO: 4; FIG. 3B). Also shown in FIG. 3 are the GEF1 domain (FIG. 3C; SEQ ID NO: 5), the BAR domain (FIG. 3D; SEQ ID NO: 6) and an unknown domain (FIG. 3E; SEQ ID NO: 7) of the native GEF1 protein of SEQ ID NO: 2. For example, the amino acid sequence of the native GEF1 protein (SEQ ID NO: 2; FIG. 3A) comprises a Pfam predicted GEF1 domain (FIG. 3A, light grey amino acid shading; PF00621) and a BAR domain (FIG. 3A, bold amino acids; PF03114). As shown in FIG. 3B, the variant GEF1 protein (SEQ ID NO: 4) is C-terminally truncated, wherein the truncation occurs near the N-terminus of the GEF1 domain (e.g., residues "VIK").

DETAILED DESCRIPTION

As set forth and described herein, the present disclosure is generally related to genetically modified filamentous fungal strains (cells) and their use in the production industrial proteins. More particularly, the present strains and methods of the disclosure relate to genetic modifications in filamentous fungi that give rise to variant strains having altered phenotypes, wherein such variant strains are particularly well-suited for growth in submerged cultures (e.g., large-scale production of proteins for industrial/commercial applications). Thus, as described herein, certain embodiments of the disclosure are related to genetically modified strains of filamentous fungus and methods thereof, wherein such modified strains comprise enhanced protein productivity phenotypes, such as improved volumetric efficiencies, higher specific productivities, improved yield on carbon sources, reduced bioreactor (fermentor) operating costs and the like.

I. Definitions

Prior to describing the present strains and methods in detail, the following terms are defined for clarity. Terms not defined should be accorded their ordinary meanings as used in the relevant art. Unless defined otherwise, all technical and scientific terms used herein have the same meaning as commonly understood by one of ordinary skill in the art to which the present compositions and methods apply.

All publications and patents cited in this specification are herein incorporated by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of $^{-}10\%$ to $^{+}10\%$ of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

In accordance with this Detailed Description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely", "only", "excluding", "not including" and the like in connection with the recitation of claim elements, or use of a "negative" limitation.

It is further noted that the term "comprising", as used herein, means "including, but not limited to", the component (s) after the term "comprising". The component(s) after the term "comprising" are required or mandatory, but the composition comprising the component(s) may further include other non-mandatory or optional component(s).

It is also noted that the term "consisting of," as used herein, means "including and limited to", the component(s) after the term "consisting of". The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

Filamentous fungus cells for manipulation, construction and use as described herein are generally from the phylum Ascomycota, subphylum Pezizomycotina, particularly fungi that have a vegetative hyphae state. Such organisms include filamentous fungus cells used for the production of commercially important industrial and pharmaceutical proteins, including, but not limited to *Trichoderma* sp., *Aspergillus* sp., *Fusarium* sp., *Penicillium* sp., *Chrysosporium* sp., *Cephalosporium* sp., *Talaromyces* sp., *Geosmithia* sp., *Neurospora* sp., *Myceliophthora* sp. and the like.

For example, in certain embodiments, filamentous fungus cells and strains thereof include, but are not limited to *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Neurospora crassa, Penicillium funiculosum, Penicillium chrysogenum, Talaromyces* (*Geosmithia*) *emersonii, Fusarium venenatum, Myceliophthora thermophila, Chrysosporium lucknowense* (C1) and the like.

As used herein, terms and phrases such as "filamentous fungus strain(s)", "filamentous fungal strain(s)", "fungus strain(s)", "fungal strains(s)", "filamentous fungus cell(s)", "filamentous fungal cell(s)", "fungus cell(s)", "fungal cell(s)" and the like may be used interchangeably for convenience of description, and are not intend to limit the scope of the disclosure.

As used herein, "yeast" and/or "yeast strains" include, but are not limited to, *Saccharomyces* sp. (e.g., *S. cerevisiae, S. pastorianus, S. carlsbergensis*), *Schizosaccharomyces* sp. (e.g., *S. pombe*), *Yarrowia* sp. (e.g., *Y. lipolytica*) and the like.

As used herein, the term "gene" is synonymous with the term "allele" in referring to a nucleic acid (polynucleotide) that encodes and directs the expression of a protein or RNA. Vegetative forms of filamentous fungi are generally haploid, therefore a single copy of a specified gene (i.e., a single allele) is sufficient to confer a specified phenotype.

As used herein, phrases such as a "parental cell", a "parental fungal cell", a "parental strain", a "parental fungal strain", a "parental strain of filamentous fungus cells", "reference strain" and the like may be used interchangeably, and refer to "unmodified" parental filamentous fungal cells. For example, a "parental strain of filamentous fungus cells" refers to any cell or strain of filamentous fungi in which the genome of the "parental" cell is modified (e.g., via a genetic modification introduced into the parental cell) to generate a variant (daughter) strain of filamentous fungus cells, such that "parental" and "daughter" cells differ.

As used herein, phrases such as a "variant cell", a "daughter cell", a "variant strain", a "daughter strain", a "variant or daughter fungal strain", a "variant or daughter strain of filamentous fungus cells" and the like may be used interchangeably, and refer to the modified strains of filamentous fungus cells that are derived (i.e., obtained from or obtainable from) from a parental (or reference) strain of filamentous fungus cells, wherein the variant strain comprises a genetic modification which is not present in the parental strain, such that, by comparison, phenotypic differences between the "parental" and "variant" strains can be attributed to the genetic modification. In other terms, parental and variant strains are otherwise isogenic except for the genetic modification(s) "introduced" into the variant strain.

Thus, parental and variant "strains" can be described as having certain characteristics, such as genetic modifications, expression phenotypes, morphology phenotypes and the like; however, the skilled person will appreciate that it is technically the "cells" of the parental or variant strain that have such characteristics, and the "strains" are referred to for convenience.

As used herein, the terms "wild-type" and "native" are used interchangeably and refer to genes, proteins, protein mixes or strains, as found in nature.

As used herein, an "endogenous filamentous fungal gene" encoding a protein of interest includes, but is not limited to, endogenous genes encoding glycoside hydrolase (GH) family enzymes (e.g., such as EC Nos. 3.2.1.1-3.2.1.206), endogenous genes encoding proteases, endogenous genes encoding esterases, endogenous genes encoding lipases and the like, as known and understood by one skilled in the art.

As used herein, the phrases "lignocellulosic degrading enzymes", "cellulase enzymes", and "cellulases" are used interchangeably, and include glycoside hydrolase (GH) enzymes such as cellobiohydrolases, xylanases, endoglucanases, and β-glucosidases, that hydrolyze the β-(1,4)-linked glycosidic bonds of cellulose (hemi-cellulose) to produce glucose.

In certain embodiments, cellobiohydrolases include enzymes classified under Enzyme Commission No. (EC 3.2.1.91), endoglucanases include enzymes classified under EC 3.2.1.4, endo-β-1,4-xylanases include enzymes classified under EC 3.2.1.8, β-xylosidases include enzymes classified under EC 3.2.1.37, and β-glucosidases include enzymes classified under EC 3.2.1.21.

As used herein, "endoglucanase" proteins may be abbreviated as "EG", "cellobiohydrolase" proteins may be abbreviated "CBH", "3-glucosidase" proteins may be abbreviated "BG" and "xylanase" proteins may be abbreviated "XYL". Thus, as used herein, a gene (or ORF) encoding a EG protein may be abbreviated "eg", a gene (or ORF) encoding a CBH protein may be abbreviated "cbh", a gene (or ORF) encoding a BG protein may be abbreviated "bg", and a gene (or ORF) encoding a XYL protein may be abbreviated "xyl".

In certain embodiments, filamentous fungus cells for manipulation, construction and use as described herein are generally from the subphylum Pezizomycotina, particularly fungi that have a vegetative hyphae state and comprise a GEF1 gene or a homologue thereof.

As used herein, a "gene or polynucleotide encoding a native GEF1 protein" comprises sequence homology to SEQ ID NO: 1. In certain embodiments, a gene or polynucleotide encoding a native GEF1 protein comprises about 70% to 100% sequence identity to SEQ ID NO: 1 or SEQ ID NO: 3. In certain other embodiments, a gene or polynucleotide encoding a native GEF1 protein comprises about 70% to 100% sequence identity to SEQ ID NO: 1 or SEQ ID NO: 3, and encodes a GEF1 domain comprising at least 90% sequence identity to SEQ ID NO: 5. In certain other embodiments, a gene or polynucleotide encoding a native GEF1 protein hybridizes with a nucleic acid sequence of SEQ ID NO: 1 or SEQ ID NO: 3, under medium to stringent hybridization conditions.

In certain embodiments, an upstream (5') cellulase gene promoter sequence includes, but is not limited to, a cellobiohydrolase (cbh) gene promoter sequence, an endoglucanase (eg) gene promoter sequence, a β-glucosidase (bg) gene promoter sequence, a xylanase (xyl) gene promoter sequence, and the like.

As used herein, an "open reading frame (ORF) nucleic acid sequence encoding a native *Trichoderma* sp. GEF1 protein" comprises sequence homology to the ORF nucleic acid sequence of SEQ ID NO: 3. In certain other embodiments, an ORF nucleic acid sequence encodes a native *Trichoderma* sp. GEF1 protein comprising about 70% to 100% sequence identity to SEQ ID NO: 2. In other embodiments, an ORF nucleic acid sequence encodes a native *Trichoderma* sp. GEF1 protein comprising about 70% to 100% sequence identity to SEQ ID NO: 2 and comprises a GEF1 domain having at least 90% sequence identity to SEQ ID NO: 5. In certain other embodiments, an ORF encoding a native GEF1 protein hybridizes with a nucleic acid sequence of SEQ ID NO: 1 or SEQ ID NO: 3 under medium to stringent hybridization conditions.

As used herein, the "position" of an amino acid residue in a "given amino acid sequence" is numbered herein using the amino acid residue numbering (positions) of the native *Trichoderma* sp. GEF1 protein of SEQ ID NO: 2. For example, FIG. 3A presents the amino acid sequence of a native *Trichoderma* sp. GEF1 protein (SEQ ID NO: 2). Thus, phrases such as "comprises a glutamic acid (E; Glu) residue at a sequence position corresponding to position 1,244 of SEQ ID NO: 2", or "comprises a GEF1 domain at a sequence position corresponding to positions 1,242-1,454 of SEQ ID NO: 2", the native (*Trichoderma* sp.) GEF1 protein's amino acid sequence (SEQ ID NO: 2) serves as a reference (parent) protein sequence. For example, as shown in FIG. 3A, a given amino acid sequence described herein can be aligned with the native *Trichoderma* sp. GEF1 protein amino acid sequence (SEQ ID NO: 2), using alignment algorithms described herein (and/or alignment algorithms known by one skilled in the art,) and an amino acid residue in the given amino acid sequence that aligns (preferably, optimally aligns) with an amino acid residue in the native sequence can be conveniently numbered by reference to the corresponding amino acid residue in the GEF1 sequence.

Likewise, to establish sequence homology or sequence identity to the primary (10) sequence of the *Trichoderma* sp. GEF1 protein (SEQ ID NO: 2), one skilled in the art may readily compare the primary sequence of SEQ ID NO: 2 with one or more candidate GEF1 protein homologue/orthologue sequences using sequence alignment algorithms, software and methods thereof know to one skilled in the art. Thus, after aligning the conserved residues, allowing for necessary insertions and deletions in order to maintain alignment (i.e., avoiding the elimination of conserved residues through arbitrary deletion and insertion), the residues equivalent to particular amino acids in the primary sequence of a candidate filamentous fungus GEF1 protein are defined. Alignment of conserved residues preferably should conserve 100% of such residues. However, alignment of greater than 98%, 95%, 90%, 85%, 80%, 75% 70%, 50% or at least 45% of conserved residues is also adequate to define equivalent residues.

As used herein, a *Trichoderma* strain named "T4" was serially propagated under selective conditions to identify and isolate mutant strains thereof capable of high temperature protein production, without adversely affecting specific productivity (Qp).

As used herein, a mutant *Trichoderma* strain named "T4-E1" (i.e., derived from parental 'T4' strain) was identified under selective temperatures and isolated, wherein T4-E1 mutant strain has a similar specific productivity (Qp) at 28° C. relative to the Qp of the T4 strain at 25° C.

As used herein, a variant *Trichoderma* strain named "T4-ΔRho #22D" was derived from the T4 parental strain, wherein the variant T4-ΔRho #22D strain comprises a pyr2 marker gene introduced at the Cas9 cleavage site (TS3) thereby disrupting the GEF1 coding sequence.

As used herein, a *Trichoderma* strain named "t-ATV84" comprises 3 copies of a *S. coccosporum* gene encoding a DXST endoglucanase and comprises deletions (or disruptions) of native cellulase genes encoding the CBHI, CBHII, EGI and EGII proteins.

As used herein, a *Trichoderma* strain named "t-AWC88" was derived from the t-ATV84 strain, and further comprises an introduced disruption of the GEF1 gene.

As used herein, the *Staphylotrichum coccosporum* endoglucanase "STCE1" has been described in U.S. Pat. No. 7,595,182 (incorporated herein by reference in its entirety).

As used herein, the "*S. coccosporum* STCE1 endoglucanase" may also be referred to as the "*S. coccosporum* DXST endoglucanase", and as such, the terms STCE1 and DXST are interchangeable. In certain embodiments, a polynucleotide sequence encoding a DXST protein is placed under the control of a promoter such as cbhI.

As used herein, the phrase "elevated fermentation (cultivation) temperatures" is a fermentation temperature greater than 25° C. In certain embodiments, an elevated fermentation temperature is at least about 25.5° C. to about 28° C. In certain embodiments, an elevated fermentation temperature is at least about 25.1° C. to 25.9° C.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins". Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure.

The term also refers to nucleotide sequences, as well as amino acid sequences. In some embodiments, analogous sequences are developed such that the replacement of amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. It is not intended that homologues necessarily be evolutionarily related. Thus, it is intended that the term encompass the same, similar, or corresponding protein(s) (i.e., in terms of structure and function) obtained from different organisms. In some embodiments, it is desirable to identify a homologue that has a quaternary, tertiary and/or primary structure similar to the reference protein.

The degree of homology between sequences can be determined using any suitable method known in the art (see, e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI); and Devereux et al., 1984).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (1987). The method is similar to that described by Higgins and Sharp (1989). Useful PILEUP parameters including a default gap weight of 3.00, a default gap length weight of 0.10, and weighted end gaps. Another example of a useful algorithm is the BLAST algorithm, described by Altschul et al., 1990 and Karlin et al., 1993. One particularly useful BLAST program is the WU-BLAST-2 program (see, e.g., Altschul et al., 1996). Parameters "W," "T," and "X" determine the sensitivity and speed of the alignment. The BLAST program uses as defaults a word-length (W) of 11, the BLOSUM62 scoring matrix (see, e.g., Henikoff and Henikoff, 1989) alignments (B) of 50, expectation (E) of 10, M'5, N'-4, and a comparison of both strands.

As used herein, the phrases "substantially similar" and "substantially identical", in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters. (See, e.g., Altschul, et al., 1990; Henikoff et al., 1989; Karlin et al., 1993; and Higgins et al., 1988). Software for performing BLAST analyses is publicly available through the National Center for Biotechnology Information. Also, databases can be searched using FASTA (Pearson et al., 1988). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to transcription, post-transcriptional modification, translation, post-translational modification, secretion and the like.

As used herein, the combined term "expresses/produces", as used in phrases such as a "variant strain of filamentous fungus cells expresses/produces an 'increased' amount of a protein of interest (POI)" (i.e., relative to the parental cell), the term "expresses/produces" is meant to include any steps involved in the expression and production of a protein in such variant filamentous fungus strains of the disclosure.

In certain embodiments, a gene, polynucleotide or nucleic acid sequence encoding a native GEF1 protein comprising "sequence homology" refers to DNA or RNA (nucleic acid) sequences that have de minimus sequence variations from the corresponding nucleic acid sequences (to which comparison is made) and retain substantially the same biological functions as the corresponding nucleic acid sequences (to which comparison is made). For example, in certain embodiments, a nucleic acid sequence comprising substantial sequence homology to a gene, polynucleotide, or nucleic acid encoding a native GEF1 protein is assessed by identifying the encoded gene product (native GEF1 protein), as described herein.

In certain other embodiments, a gene, polynucleotide, or nucleic acid sequence comprising sequence homology to a gene, polynucleotide, or nucleic acid encoding a native GEF1 protein is determined/identified using nucleic acid hybridization methods. For example, in certain embodiments, a DNA/RNA sequence comprising substantial sequence homology to a gene encoding a native GEF1 protein (e.g., SEQ ID NO: 2) is identified by the ability of such DNA/RNA sequence to hybridize with a specified nucleic acid sequence of the disclosure, under stringent conditions.

As used herein, "hybridizes under stringent conditions" is intended to describe conditions for hybridization and washing under which nucleotide sequences that are significantly identical or homologous to each other remain hybridized to each other. Such stringent conditions are well known to those skilled in the art (see, e.g., Ausubel et al., 1995; Sambrook et al., 1989). For example, in certain embodiments, a non-limiting example of stringent hybridization conditions includes hybridization in 4× sodium chlorine/ sodium citrate (SSC), at about 65-70° C. (or hybridization in 4×SSC plus 50% formamide at about 42-50° C.), followed by one or more washes in 1×SSC, at about 65-70° C. Likewise, anon-limiting example of highly stringent hybridization conditions includes hybridization in 1×SSC, at about 65-70° C. (or hybridization in 4×SSC plus 50% formamide at about 42-50° C.), followed by one or more washes in 0.3×SSC, at about 65-70° C. Thus, highly stringent hybridization conditions include hybridization in 4×SSC, at about 50-60° C. (or alternatively hybridization in 6×SSC plus 50% formamide at about 40-45° C.), followed by one or more washes in 2×SSC, at about 50-60° C. Ranges intermediate to the above-recited values, e.g., at 65-70° C. or at 42-50° C. are also intended to be encompassed by the present disclosure. In certain embodiments, SSPE (1×SSPE is 0.15 M NaCl, 10 mM NaH2PO4, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional, non-limiting example of stringent hybridization conditions is hybridization in 0.25-0.5M NaH2PO4, 7% SDS at about 65° C., followed by one or more washes at 0.02M NaH2PO4, 1% SDS at 65° C. or alternatively 0.2×SSC, 1% SDS (see, e.g., Church and Gilbert, 1984).

Thus, as generally set forth above, certain embodiments of the disclosure are related to variant strains of filamentous fungus cells comprise a genetic modification of a gene encoding a native GEF1 protein. As used herein, the terms "modification" and "genetic modification" are used interchangeably and include, but are not limited to: (a) the introduction, substitution, or removal of one or more nucleotides in a gene, or the introduction, substitution, or removal of one or more nucleotides in a regulatory element required for the transcription or translation of the gene, (b) gene disruption, (c) gene conversion, (d) gene deletion, (e) the down-regulation of a gene (e.g., antisense RNA, siRNA, miRNA, and the like), (f) specific mutagenesis (including, but not limited to, CRISPR/Cas9 based mutagenesis) and/or (g) random mutagenesis of any one or more the genes disclosed herein.

As used herein, a variant strain of filamentous fungus comprising a genetic modification includes, but is not limited to a genetic modification of a gene encoding a native GEF1 protein disclosed herein.

Thus, as described in further detail below, various molecular biological methods are well known and available to one skilled in the art for generating/constructing such variant strains of filamentous fungus cells.

As used herein, "the introduction, substitution, or removal of one or more nucleotides in a gene encoding a protein", such genetic modifications include the gene's coding sequence (i.e., exons) and non-coding intervening (introns) sequences.

As used herein, "disruption of a gene", "gene disruption", "inactivation of a gene" and "gene inactivation" are used interchangeably and refer broadly to any genetic modification that substantially disrupts/inactivates a target gene. Exemplary methods of gene disruptions include, but are not limited to, the complete or partial deletion of any portion of a gene, including a polypeptide coding sequence (CDS), a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the expression/production of the functional gene product. In certain embodiments of the disclosure, such gene disruptions prevent a host cell from expressing/producing the encoded lov gene product.

In certain embodiments, a gene, polynucleotide or nucleic acid sequence encoding a native GEF1 protein is genetically modified using an established gene editing technique, such as CRISPR/Cas9 gene editing, zinc-finger nuclease (ZFN) gene editing, transcription activator-like effector nuclease editing (TALEN), homing (mega) nuclease editing, and the like.

In other embodiments, a variant strain of filamentous fungus is constructed (i.e., genetically modified) by the process of gene conversion (e.g., see Iglesias and Trautner, 1983).

In other embodiments, a protein of interest (e.g., an endogenous POI or a heterologous POI) expressed/produced by the fungal cells of the disclosure is detected, measured, assayed and the like, by protein quantification methods, gene transcription methods, mRNA translation methods and the like, including, but not limited to protein migration/mobility (SDS-PAGE), mass spectrometry, HPLC, size exclusion, ultracentrifugation sedimentation velocity analysis, transcriptomics, proteomics, fluorescent tags, epitope tags, fluorescent protein (GFP, RFP, etc.) chimeras/hybrids and the like.

As used herein, functionally and/or structurally similar proteins are considered to be "related proteins". Such related proteins can be derived from organisms of different genera and/or species, or even different classes of organisms (e.g., bacteria and fungi). Related proteins also encompass homologues and/or orthologues determined by primary sequence analysis, determined by secondary or tertiary structure analysis, or determined by immunological cross-reactivity.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter).

Coding sequences can be operably linked to regulatory sequences in sense or antisense orientation. A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a fungal cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection and the like.

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in the cell that is to be transformed).

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the fungal cell chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene.

In alternative embodiments, the incoming sequence encodes a functional wild-type gene or operon, a functional mutant gene or operon, or a nonfunctional gene or operon. In some embodiments, an incoming sequence is a non-functional sequence inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the fungal cell chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the fungal cell chromosome a DNA construct is integrated and directs what part of the fungal cell chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As defined herein, a host cell "genome", a fungal cell "genome", or a filamentous fungus cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "vector" refers to any nucleic acid that can be replicated (propagated) in cells and can carry new genes or DNA segments (e.g., an "incoming sequence") into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously) or can integrate into the chromosome of a host cell.

A used herein, a "transformation cassette" refers to a specific vector comprising a gene (or ORF thereof), and having elements in addition to the gene that facilitate transformation of a particular host cell.

As used herein, "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing genetic modifications into the chromosome of a host cell through homologous recombination.

In some embodiments, a targeting vector comprises other non-homologous sequences, e.g., added to the ends (i.e., stuffer sequences or flanking sequences). The ends can be closed such that the targeting vector forms a closed circle, such as, for example, insertion into a vector.

As used herein, a variant cell (or strain) comprising an "enhanced protein productivity phenotype" includes, but is not limited to, a variant cell (or strain) comprising an enhanced/increased volumetric productivity, a variant cell (or strain) comprising an enhanced/increased carbon conversion efficiency, a variant cell (or strain) comprising an enhanced/increased protein yield, a variant cell (or strain) comprising an enhanced/increased specific protein productivity and the like. For example, in certain embodiments, a variant cell or strain comprising an enhanced protein productivity phenotype expresses/produces at least 0.1% or more total protein (g) per g of fed sugars (relative to parental strain), wherein fed sugars can be expressed in terms of mass of sugar added to the fermentor during production phase (i.e., following feed-start).

As defined herein, the phrases "enhanced protein productivity phenotype" and "increased protein productivity phenotype", may be used interchangeably.

As used herein, when describing an "enhanced/increased protein productivity phenotype" in an unmodified (parental) cell vis-à-vis the modified (variant/daughter), it will be understood that the "parental" and "variant" cells are grown/cultivated/fermented under the same conditions (e.g., the same conditions such as media, temperature, pH and the like). Similarly, when describing the "expression/production" of a protein of interest (POI) in an unmodified (parental) cell vis-à-vis the "expression/production" of the same POI in a modified (variant/daughter) cell, it will be understood that the "parental" and "variant" cells are grown/cultivated/fermented under essentially the same conditions (e.g., the same conditions such as media, temperature, pH and the like).

As used herein, "aerobic fermentation" refers to growth in the presence of oxygen.

As used herein, the terms "broth", "cell broth", "fermentation broth" and/or "culture broth" are used interchangeably, and refer collectively to (i) the fermentation (culture) medium and (ii) the cells, in a liquid (submerged) culture.

As used herein, the term "cell mass" refers to the cell component (including intact and lysed cells) present in a liquid (submerged) culture. Cell mass can be expressed in dry cell weight (DCW) or wet cell weight (WCW).

II. Fungal Strains Comprising Enhanced Protein Productivity Phenotypes at Elevated Cultivation Temperatures As generally described and set forth below in the Examples section, Applicant serially propagated a *Trichoderma reesei* whole cellulase strain named T4 under selective conditions to identify and isolate mutant strains thereof capable of high temperature protein production (i.e., without adversely affecting specific productivity ($Q_p$); e.g., see Example 1). More particularly, a mutant *T. reesei* strain named "T4-E1" was identified and isolated under such selective conditions (Example 2), wherein the mutant T4-E1 strain has a similar specific productivity at 28° C., relative to the parental T4 strain at 25° C. (TABLE 1). Applicant identified the mutated gene in the T4-E1 strain, wherein the deduced amino acid sequence of the encoded protein (SEQ ID NO: 2; PID: 120482) includes a region of sequence homology with a GEF1 protein domain (SEQ ID NO: 5). As detailed in Example 2, the mutation in the T4-E1 strain replaced a glutamate codon (Glu; amino acid position 1,245) with a pre-mature stop codon, which thereby truncated the (GEF1) protein near the beginning of the "GEF1 domain" (e.g., see FIG. 3A native sequence versus FIG. 3B C-terminally truncated sequence).

As described in Example 3 of the disclosure, Applicant further constructed a variant (modified) *Trichoderma* strain (named "T4-ΔRho #22D") derived from the T4 parental strain, wherein the variant T4-ΔRho #22D strain comprises a pyr2 marker gene introduced at the Cas9 cleavage site (TS3), thereby disrupting the GEF1 coding sequence. For example, the fermenter (cultivation) performance of the wild-type (parental) T4 strain, the mutant T4-E1 strain and the constructed variant T4-ΔRho #22D strain are presented in TABLE 1, wherein the mutant T4-E1 strain and the constructed variant T4-ΔRho #22D strain demonstrate increased total protein production rates at 28° C., relative to the parental T4 strain total protein production rate at 25° C.

As further described in Example 4, Applicant constructed a *Trichoderma* sp. production strain transformed with copies of the gene encoding a *S. coccosporum* DXST (STCE1) endoglucanase. More particularly, a parental *Trichoderma* DXST production strain named "t-ATV84" was transformed with copies of the gene encoding a *S. coccosporum* DXST endoglucanase and further comprises deletions of native cellulase genes encoding the CBHI, CBHII, EGI and EGII proteins. Likewise, the variant (modified) *Trichoderma* DXST production strain named "t-AWC88" was derived from the t-ATV84 strain, and further comprises an introduced disruption of the GEF1 gene. For example, as shown in TABLE 2, the variant *Trichoderma* strain (t-AWC88) comprising the disrupted GEF1 gene demonstrates a higher amount of DXST endoglucanase produced at 25° C., 26° C. and 27° C., relative to the amount of DXST endoglucanase produced by the parental strain (t-ATV84) at 25° C., which comprises the native GEF1 gene.

III. Molecular Biology

As generally set forth above, certain embodiments of the disclosure are related to modified filamentous fungal strains comprising enhanced protein productivity phenotypes. In certain preferred embodiments, the modified (variant) filamentous fungal strains comprise enhanced protein productivity phenotypes at elevated fermentation (cultivation) temperatures. In another embodiment, the disclosure is related to modified yeast strains comprising enhanced ethanol productivity phenotypes. In certain preferred embodiments, the modified (variant) yeast strains comprise enhanced ethanol productivity phenotypes at elevated fermentation (cultivation) temperatures.

Thus, certain other embodiments of the disclosure are related to molecular biology, genetic modifications, polynucleotides, genes, ORFs, vectors, expression cassettes, and the like. In certain embodiments, the disclosure is related to recombinant nucleic acids (polynucleotides) comprising a gene or ORF encoding a protein of interest (POI). In certain embodiments, a recombinant nucleic acid (polynucleotide) comprises a polynucleotide expression cassette encoding a POI.

In certain embodiments, a polynucleotide of the disclosure comprises one or more selectable markers. Selectable markers for use in filamentous fungi include, but are not limited to, als1, amdS, hygR, pyr2, pyr4, pyrG, sucA, a bleomycin resistance marker, a blasticidin resistance marker, a pyrithiamine resistance marker, a chlorimuron ethyl resistance marker, a neomycin resistance marker, an adenine pathway gene, a tryptophan pathway gene, a thymidine kinase marker and the like. In a particular embodiment, the selectable marker is pyr2, which compositions and methods of use are generally set forth in PCT Publication No. WO2011/153449.

Standard techniques for transformation of filamentous fungi and culturing the fungi (which are well known to one skilled in the art) are used to transform a fungal host cell of the disclosure. Thus, the introduction of a DNA construct or vector into a fungal host cell includes techniques such as transformation, electroporation, nuclear microinjection, transduction, transfection (e.g., lipofection mediated and DEAE-Dextrin mediated transfection), incubation with calcium phosphate DNA precipitate, high velocity bombardment with DNA-coated micro-projectiles, gene gun or biolistic transformation, protoplast fusion and the like. General transformation techniques are known in the art (see, e.g., Ausubel et al., 1987, Sambrook et al., 2001 and 2012, and Campbell et al., 1989). The expression of heterologous proteins in *Trichoderma* is described, for example, in U.S. Pat. Nos. 6,022,725; 6,268,328; Harkki et al., 1991 and Harkki et al., 1989. Reference is also made to Cao et al. (2000) for transformation of *Aspergillus* strains.

Generally, transformation of *Trichoderma* sp. uses protoplasts or cells that have been subjected to a permeability treatment, typically at a density of $10^5$ to $10^7$/mL, particularly $2\times10^6$/mL. A volume of 100 L of these protoplasts or cells in an appropriate solution (e.g., 1.2 M sorbitol and 50 mM $CaCl_2$) is mixed with the desired DNA. Generally, a high concentration of polyethylene glycol (PEG) is added to the uptake solution. Additives, such as dimethyl sulfoxide, heparin, spermidine, potassium chloride and the like, may also be added to the uptake solution to facilitate transformation. Similar procedures are available for other fungal host cells (e.g., see U.S. Pat. Nos. 6,022,725 and 6,268,328, both of which are incorporated by reference.

Thus, the methods and compositions of instant disclosure generally rely on routine techniques in the field of recombinant genetics. For example, in certain embodiments, a heterologous gene or ORF encoding a protein of interest is introduced into a filamentous fungal (host) cell. In certain embodiments, the heterologous gene or ORF is typically cloned into an intermediate vector, before being transformed into a filamentous fungal (host) cells for replication and/or expression. These intermediate vectors can be prokaryotic vectors, such as, e.g., plasmids, or shuttle vectors. In certain embodiments, the expression of the heterologous gene or ORF is under the control of its native promoter. In other embodiments, the expression of the heterologous gene or ORF is placed under the control of a heterologous promoter, which can be a heterologous constitutive promoter or a heterologous inducible promoter.

Those skilled in the art are aware that a natural (native) promoter can be modified by replacement, substitution, addition or elimination of one or more nucleotides, without changing its function. The practice of the invention encompasses but is not constrained by such alterations to the promoter.

The expression vector typically contains a transcription unit or "expression cassette" that contains all the additional elements required for the expression of the heterologous sequence. For example, a typical expression cassette contains a 5' promoter operably linked to a heterologous nucleic acid sequence encoding a protein of interest and may further comprise sequence signals required for efficient polyadenylation of the transcript, ribosome binding sites, and translation termination sequences. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes. Although any fungal terminator is likely to be functional in the present invention, preferred terminators include: the terminator from *Trichoderma* cbhI gene, the terminator from *Aspergillus nidulans* trpC gene (Yelton et al., 1984; Mullaney et al., 1985) and the *Aspergillus awamori* or *Aspergillus niger* glucoamylase genes (Nunberg et al., 1984; Boel et al., 1984).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that can be included in expression vectors may also be a replicon, a gene encoding antibiotic resistance to permit selection of bacteria that harbor recombinant plasmids, or unique restriction sites in nonessential regions of the plasmid to allow insertion of heterologous sequences. The particular antibiotic resistance gene chosen is not dispositive either, as any of the many resistance genes known in the art may be suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of the filamentous fungus. However, transformation resulting in the maintenance of a self-replicating extra-chromosomal transformation vector is also contemplated. Many standard transfection methods can be used to produce *Trichoderma reesei* cell lines that express large quantities of the heterologous protein, and as such, any of the known procedures for introducing foreign nucleotide sequences into fungal host cells may be used. These include the use of calcium phosphate transfection, polybrene, protoplast fusion, electroporation, biolistics, liposomes, microinjection, plasma vectors, viral vectors and any of the other known methods for introducing cloned genomic DNA, cDNA, synthetic DNA or other foreign genetic material into a host cell. Also of use is the *Agrobacterium*-mediated transfection method such as the one described in U.S. Pat. No. 6,255,115.

After the expression vector is introduced into the cells, the transformed cells are cultured under conditions favoring expression of gene. Large batches of transformed cells can be cultured as described herein. Finally, the protein product is recovered from the culture using standard techniques. Thus, the disclosure herein provides for the expression and enhanced production of desired proteins of interest, particularly at elevated fermentation (cultivation) temperatures described herein.

In certain other embodiments, the disclosure is related genetically modified filamentous fungal strains (cells) comprising enhanced protein productivity phenotypes. In particular embodiments, a modified fungal strain of the disclosure comprised an enhanced protein productivity phenotype at elevated fermentation temperatures. For example, in certain embodiments, a variant strain of filamentous fungus comprises genetic modification of a gene encoding a GEF1 protein, wherein the genetic modification includes, but is not limited to: (a) the introduction, substitution, or removal of one or more nucleotides in the GEF1 gene (or ORF thereof), or the introduction, substitution, or removal of one or more nucleotides in a regulatory element required for the transcription or translation of the GEF1 gene (or ORF thereof), (b) a gene disruption, (c) a gene conversion, (d) a gene deletion, (e) a gene down-regulation, (f) specific mutagenesis and/or (g) random mutagenesis of a gene encoding a GEF1 protein comprising sequence identity to SEQ ID NO: 2.

Thus, in certain embodiments, a variant strain of filamentous fungus comprising a genetic modification is constructed by gene deletion to eliminate the expression/production of the GEF1 protein.

In other embodiments, a variant strain of filamentous fungus comprising a genetic modification is constructed by partial gene deletion or gene disruption to eliminate the expression/production of the native GEF1 protein. For example, as set forth below in the Example 3 (FIG. 3B), inactivation of the native GEF1 gene in a parental filamentous fungal strain, by introducing a pre-mature stop codon (i.e., which C-terminally truncates the GEF1 protein; SEQ ID NO: 4), resulted in a variant (daughter) strain comprising an enhanced protein productivity phenotype relative to the parental cell when fermented at 25° C. More particularly, when the parental (T4) and daughter (T4-ΔRho #22D) strains were fermented at an elevated fermentation temperature (28° C.), the variant (daughter) strain demonstrated an increased protein productivity phenotype (TABLE 1, protein production rate) relative to the parental strain.

Thus, in certain embodiments, a modified filamentous fungal strain comprises a partial deletion of the GEF1 gene, wherein a partial deletion includes the partial deletion of any portion of the GEF1 gene's coding sequence, wherein such variant strain comprises an enhanced protein productivity phenotype. Thus, in certain other embodiments, such variant strains do not express/produce the GEF1 protein, or such variant strains express/produce a reduced amount of the GEF1 protein relative to the parental strain.

Thus, as generally set forth herein and described above, one skilled in the art may readily perform one or more genetic modifications and construct variant filamentous fungus strains thereof, by reference to one or more nucleic acid sequences and/or protein sequence disclosed herein.

For example, gene deletion techniques enable the partial or complete removal of the gene, thereby eliminating or reducing expression/production of the protein, and/or thereby eliminating or reducing expression/production the encoded protein (e.g., GEF1). In such methods, the deletion of the gene may be accomplished by homologous recombination using an integration plasmid/vector that has been constructed to contiguously contain the 5' and 3' regions flanking the gene. The contiguous 5' and 3' regions may be introduced into a filamentous fungal cell, for example, on an integrative plasmid/vector in association with a selectable marker to allow the plasmid to become integrated in the cell.

In other embodiments, a variant strain of filamentous fungus comprises genetic modification which disrupts or inactivates the gene encoding the protein (e.g., GEF1). Exemplary methods of gene disruption/inactivation include disrupting any portion of the gene (e.g., see, FIG. 1-FIG. 3), including the polypeptide coding sequence (CDS), promoter, enhancer, or another regulatory element, which disruption includes substitutions, insertions, deletions, inversions, and combinations thereof and variations thereof. A non-limiting example of a gene disruption technique includes inserting (integrating) into one or more of the genes of the disclosure an integrative plasmid containing a nucleic acid fragment homologous to the (e.g., GEF1) gene, which will create a duplication of the region of homology and incorporate (insert) vector DNA between the duplicated regions. In certain other non-limiting examples, a gene disruption technique includes inserting into a gene (e.g., a gene encoding a GEF1 protein) an integrative plasmid containing a nucleic acid fragment homologous to the (e.g., GEF1) gene, which will create a duplication of the region of homology and incorporate (insert) vector DNA between the duplicated regions, wherein the vector DNA inserted separates, e.g., the promoter of the GEF1 gene from the GEF1 protein coding region, or interrupts (disrupts) the coding, or non-coding, sequence of the GEF1 gene, resulting in an enhanced protein productivity phenotype. Thus, a disrupting construct may be a selectable marker gene (e.g., pyr2) accompanied by 5' and 3' regions homologous to the GEF1 gene. The selectable marker enables identification of transformants containing the disrupted gene. Thus, in certain embodiments, gene disruption includes modification of control elements of the gene, such as the promoter, ribosomal binding site (RBS), untranslated regions (UTRs), codon changes, and the like.

In other embodiments, a variant strain of filamentous fungus is constructed (i.e., genetically modified) by introducing, substituting, or removing one or more nucleotides in the gene, or a regulatory element required for the transcription or translation thereof. For example, nucleotides may be inserted or removed so as to result in the introduction of a pre-mature stop codon, the removal of the start codon, or a frame-shift of the open reading frame (ORF). Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990).

In another embodiment, a variant strain of filamentous fungus is constructed by the process of gene conversion (e.g., see Iglesias and Trautner, 1983). For example, in the gene conversion method, a nucleic acid sequence corresponding to the target gene is mutagenized in vitro to produce a defective nucleic acid sequence, which is then transformed into the parental cell to produce a variant cell comprising a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993).

In other embodiments, a variant strain of filamentous fungus is constructed by established anti-sense (gene-silencing) techniques, using a nucleotide sequence complementary to the nucleic acid sequence of the GEF1 gene (Parish and Stoker, 1997). More specifically, expression of a gene by a filamentous fungus strain may be reduced (down-regulated) or eliminated by introducing a nucleotide sequence complementary to the nucleic acid sequence of the gene, which is transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a variant strain of filamentous fungus is constructed by random or specific mutagenesis using methods well known in the art, including, but not limited to, chemical mutagenesis and transposition (see, e.g., Youngman et al., 1983). Modification of the gene may be performed by subjecting the parental cell to mutagenesis and screening for mutant cells in which expression of the GEF1 gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods. Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

In certain other embodiments, a variant strain of filamentous fungus is constructed by means of site specific gene editing techniques. For example, in certain embodiments, a variant strain of filamentous fungus is constructed (i.e., genetically modified) by use of transcriptional activator like endonucleases (TALENs), zinc-finger endonucleases (ZFNs), homing (mega) endonuclease and the like. More particularly, the portion of the gene to be modified (e.g., a coding region, a non-coding region, a leader sequence, a pro-peptide sequence, a signal sequence, a transcription terminator, a transcriptional activator, or other regulatory elements required for expression of the coding region) is subjected genetic modification by means of ZFN gene editing, TALEN gene editing, homing (mega) endonuclease and the like, which modification methods are well known and available to one skilled in the art.

In certain other embodiments, a variant strain of filamentous fungus is constructed by means of CRISPR/Cas9 editing (e.g., see Examples herewith). More specifically, compositions and methods for fungal genome modification by CRISPR/Cas9 systems are described and well known in the art (e.g., see, PCT Publication Nos: WO2016/100571, WO2016/100568, WO2016/100272, WO2016/100562 and the like). Thus, a gene encoding a GEF1 protein can be disrupted, deleted, mutated or otherwise genetically modified by means of nucleic acid guided endonucleases, that find their target DNA by binding either a guide RNA (e.g., Cas9) or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (e.g., a Cas9 from *S. pyogenes*, or a codon optimized gene encoding the Cas9 nuclease) is operably linked to a promoter active in the filamentous fungal cell and a terminator active in filamentous fungal cell, thereby creating a filamentous fungal Cas9 expression cassette. Likewise, one or more target sites unique to the gene of interest are readily identified by a person skilled in the art.

For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a filamentous fungal expression cassette for the gRNA is created by operably linking the DNA encoding the gRNA to a promoter active in filamentous fungal cells and a terminator active in filamentous fungal cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the filamentous fungal host's machinery to repair the DNA break generated by the RGEN (RNA-guided endonuclease).

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR, by amplifying the target locus with a forward and reverse primer. These primers can amplify the wild-type locus or the modified locus that has been edited by the RGEN. These fragments are then sequenced using a sequencing primer to identify edited colonies.

Another way in which a gene encoding a GEF1 protein of the disclosure can be genetically modified is by altering the expression level of the gene of interest. For example, nuclease-defective variants of such nucleotide-guided endonucleases (e.g., Cas9 D10A, N863A or Cas9 D10A, H840A) can be used to modulate gene expression levels by enhancing or antagonizing transcription of the target gene. These Cas9 variants are inactive for all nuclease domains present in the protein sequence, but retain the RNA-guided DNA binding activity (i.e., these Cas9 variants are unable to cleave either strand of DNA when bound to the cognate target site). Thus, the nuclease-defective proteins (i.e., Cas9 variants) can be expressed as a filamentous fungus expression cassette and when combined with a filamentous fungus gRNA expression cassette, such that the Cas9 variant protein is directed to a specific target sequence within the cell. The binding of the Cas9 (variant) protein to specific gene target sites can block the binding or movement of transcription machinery on the DNA of the cell, thereby decreasing the amount of a gene product produced. Thus, any of the genes disclosed herein can be targeted for reduced gene expression using this method. Gene silencing can be monitored in cells containing the nuclease-defective Cas9 expression cassette and the gRNA expression cassette(s) by using methods such as RNAseq.

V. Proteins of Interest

As briefly stated in the preceding sections, the present strains and methods find use in the production of commercially important proteins in submerged cultures of filamentous fungi. A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

In certain embodiments, a variant strain of filamentous fungus exhibits an increased protein titer relative to the (unmodified) parental strain, wherein protein titer is defined as the amount of protein per volume (g/L). For example, titers can be measured by methods known in the art (e.g., ELISA, HPLC, Bradford assay, LC/MS and the like). Thus, in certain embodiments, a variant strain of filamentous fungus comprises a protein titer increase of at least about 0.1%, at least about 1%, at least about 5%, at least about 6%, at least about 7%, at least about 8%, at least about 9%, or at least about 10% or more as compared to the unmodified (parental) cell.

In certain embodiments, a variant strain of filamentous fungus exhibits an increased volumetric productivity relative to the (unmodified) parental strain, wherein volumetric productivity is defined as the amount of protein produced (g) during the fermentation per nominal volume (L) of the bioreactor per total fermentation time (h). For example, volumetric productivities can be measured by methods know in the art (e.g., ELISA, HPLC, Bradford assay, LC/MS and the like). Thus, in certain embodiments, a variant strain of filamentous fungus comprises a volumetric productivity increase of at least about 0.1%, at least about 1%, at least about 5%, at least about 6%, at least about 7%, at least about 8%, at least about 9%, or at least about 10% or more as compared to the unmodified (parental) cell.

In certain other embodiments, a variant strain of filamentous fungus exhibits an increased total protein yield, wherein total protein yield is defined as the amount of protein produced (g) per gram of carbohydrate fed, relative to the (unmodified) parental strain. Thus, as used herein, total protein yield (g/g) may be calculated using the following equation:

$$Y_f = T_p / T_c$$

wherein "$Y_f$" is total protein yield (g/g), "$T_p$" is the total protein produced during the fermentation (g) and "$T_c$" is the total carbohydrate (g) fed during the fermentation (bioreactor) run. In certain embodiments, the increase in total protein yield of the modified strain (i.e., relative to the parental strain) is an increase of at least about 0.1%, at least about 1%, at least about 5%, at least about 6%, at least about 7%, at least about 8%, at least about 9%, or at least about 10% or more as compared to the unmodified (parental) cell.

Total protein yield may also be described as carbon conversion efficiency/carbon yield, for example, as in the percentage (%) of carbon fed that is incorporated into total protein. Thus, in certain embodiments, a variant strain of filamentous fungus comprises an increased carbon conversion efficiency (e.g., an increase in the percentage (%) of carbon fed that is incorporated into total protein), relative to the (unmodified) parental strain. In certain embodiments, the increase in carbon conversion efficiency of the modified strain (i.e., relative to the parental strain) is an increase of at least about 0.1%, at least about 1%, at least about 5%, at least about 6%, at least about 7%, at least about 8%, at least about 9%, or at least about 10% or more as compared to the unmodified (parental) cell.

In certain embodiments, a variant strain of filamentous fungus exhibits an increased specific productivity (Qp) of a POI relative the (unmodified) parental strain. For example, the detection of specific productivity (Qp) is a suitable method for evaluating rate of protein production. The specific productivity (Qp) can be determined using the following equation:

"$Qp$=gP/gDCW·hr"

wherein, "gP" is grams of protein produced in the tank; "gDCW" is grams of dry cell weight (DCW) in the tank and "hr" is fermentation time in hours from the time of inoculation, which includes the time of production as well as growth time. Thus, in certain embodiments, a variant strain of filamentous fungus comprises a specific productivity (Qp) increase of at least about 0.1%, at least about 1%, at least about 5%, at least about 6%, at least about 7%, at least about 8%, at least about 9%, or at least about 10% or more as compared to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

In certain embodiments, a POI or a variant POI thereof is selected from an Enzyme Commission (EC) Number selected from the group consisting of EC 1, EC 2, EC 3, EC 4, EC 5 or EC 6.

For example, in certain embodiments a POI is an oxidoreductase enzyme, including, but not limited to, an EC1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase), EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease Si), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1, 6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-O-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetylglucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.—(e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase).

These and other aspects and embodiments of the present strains and methods will be apparent to the skilled person in view of the present description and the following Examples.

VII. Fermentation

In certain embodiments, the disclosure provides methods for producing a protein of interest comprising fermenting a filamentous fungal cell, wherein the fungal cell secrets the protein of interest. In other embodiments, the disclosure provides methods for producing increased amounts of ethanol in a yeast strain. In general, fermentation methods well known in the art are used to ferment the fungal cells. In some embodiments, the fungal cells are grown under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within batch cultures, cells progress through a static lag phase to a high growth log phase and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Certain embodiments of the instant disclosure are related to fermentation procedures for culturing fungi. Fermentation procedures for production of cellulase enzymes are known in the art. For example, cellulase enzymes can be produced either by solid or submerged culture, including batch, fed-batch and continuous-flow processes. Culturing is generally accomplished in a growth medium comprising an aqueous mineral salts medium, organic growth factors, a carbon and energy source material, molecular oxygen, and, of course, a starting inoculum of the filamentous fungal host to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. Preferences for pH range of microorganisms are dependent on the media employed to some extent, as well as the particular microorganism, and thus change somewhat with change in media as can be readily determined by those skilled in the art.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this level is not critical and may vary with the particular microorganism and fermentation process being conducted. However, it is well known in the art how to determine the carbon source concentration in the fermentation medium and whether or not the desired level of carbon source has been achieved.

The fermentation can be conducted as a batch or continuous operation, fed batch operation is much to be preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermenter.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermenter, cell density measurable by dry cell weights, light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermenter employed is not critical.

The collection and purification of proteins from the fermentation broth can also be done by procedures known to one of skill in the art. The fermentation broth will generally contain cellular debris, including cells, various suspended solids and other biomass contaminants, as well as the desired cellulase enzyme product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate, followed by purification by a variety of chromatographic procedures, e.g., ion exchange chromatography, affinity chromatography or similar art recognized procedures.

VIII. Exemplary Embodiments

Non-limiting embodiments of the disclosure include, but are not limited to:

1. A variant (or modified) strain of filamentous fungus derived from a parental filamentous fungus strain comprising a gene encoding a native GEF1 protein, wherein the variant strain comprises a genetic modification which disrupts or deletes the gene encoding the native GEF1 protein, wherein the variant strain comprises an enhanced protein productivity phenotype relative to the parental strain when cultivated under the same conditions.
2. The variant strain of embodiment 1, wherein the enhanced protein productivity phenotype is selected from the group consisting of increased protein productivity, increased total protein productivity, increased volumetric productivity, increased carbon conversion efficiency and increased specific productivity.

3. The variant strain of embodiment 1, wherein the filamentous fungus is a Pezizomycotina.

4. The variant strain of embodiment 1, wherein the filamentous fungus is selected from the group consisting of a *Trichoderma* sp. strain, *Aspergillus* sp. strain, *Fusarium* sp. strain, *Penicillium* sp. strain, a *Candida* sp. strain, *Chrysosporium* sp. strain, *Cephalosporium* sp. strain, *Talaromyces* sp. strain, *Neurospora* sp. strain and *Myceliophthora* sp. strain.

5. The variant strain of embodiment 1, comprising an increased protein productivity phenotype relative to the parental strain when the variant and parental strains are fermented under the same conditions at 25° C.

6. The variant strain of embodiment 1, comprising an increased protein productivity phenotype relative to the parental strain when the variant and parental strains are fermented under the same conditions at 26° C.

7. The variant strain of embodiment 1, comprising an increased protein productivity phenotype relative to the parental strain when the variant and parental strains are fermented under the same conditions at 27° C.

8. The variant strain of embodiment 1, comprising an increased protein productivity phenotype relative to the parental strain when the variant and parental strains are fermented under the same conditions at 28° C.

9. The variant strain of embodiment 1, comprising a gene encoding an endogenous protein of interest (POI).

10. The variant strain of embodiment 9, wherein the endogenous POI is a lignocellulosic degrading enzyme.

11. The variant strain of embodiment 1, comprising an expression construct encoding a heterologous protein of interest (POI).

12. The variant strain of embodiment 11, wherein the heterologous POI is selected from an enzyme, an antibody or a fragment thereof, a receptor protein and a peptide.

13. The variant strain of embodiment 12, wherein the heterologous POI is an enzyme selected from the group consisting of oxidoreductases, transferases, hydrolases, lyases, isomerases and ligases.

14. The variant strain of embodiment 12, wherein the heterologous POI is an enzyme selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, and hexose oxidases.

15. A protein of interest produced by the variant strain of embodiment 1.

16. The variant strain of embodiment 1, wherein the encoded GEF1 protein comprises at least 70% sequence identity to SEQ ID NO: 2.

17. The variant strain of embodiment 1, wherein the encoded GEF1 protein comprises at least 90% sequence identity to the GEF1 domain of SEQ ID NO: 5.

18. The variant strain of embodiment 1, wherein the gene encoding the GEF1 protein comprises at least 70% sequence identity to the GEF1 polynucleotide sequence of SEQ ID NO: 1.

19. The variant strain of embodiment 1, wherein the gene encoding the GEF1 protein comprises at least 70% sequence identity to the open reading frame (ORF) sequence of SEQ ID NO: 3.

20. The variant strain of embodiment 1, wherein the gene encoding the GEF1 protein hybridizes with a GEF1 gene of SEQ ID NO: 1, or the GEF1 ORF of SEQ ID NO: 3, under medium to stringent hybridization conditions.

21. The variant strain of embodiment 1, wherein the genetic modification truncates at least the first 20 amino acid residues of the GEF1 N-terminus, or truncates at least the last 20 amino acid residues of the GEF1 C-terminus.

22. The variant strain of embodiment 1, wherein the genetic modification truncates at least the first 200 amino acid residues of the GEF1 N-terminus, or truncates at least the last 200 amino acid residues of the GEF1 C-terminus.

23. The variant strain of embodiment 1, wherein the genetic modification truncates at least the first 500 amino acid residues of the GEF1 N-terminus, or truncates at least the last 500 amino acid residues of the GEF1 C-terminus.

24. The variant strain of embodiment 1, wherein the genetic modification truncates at least 700 to 750 amino acid residues of the GEF1 C-terminus.

25. The variant strain of embodiment 1, wherein the gene encoding the GEF1 protein is deleted.

26. A method for producing an increased amount of an endogenous protein of interest (POI) in a modified filamentous fungal strain comprising (a) genetically modifying a filamentous fungal strain by disrupting or deleting the native GEF1 gene, and (b) fermenting the modified strain under suitable conditions for the production of the POI, wherein the modified strain produces an increased amount of the POI relative to the parental strain when cultivated under the same conditions at 25° C.

27. The method of embodiment 26, wherein the filamentous fungus is a Pezizomycotina.

28. The method of embodiment 26, wherein the filamentous fungus is selected from the group consisting of a *Trichoderma* sp. strain, *Aspergillus* sp. strain, *Fusarium* sp. strain, *Penicillium* sp. strain, a *Candida* sp. strain, *Chrysosporium* sp. strain, *Cephalosporium* sp. strain, *Talaromyces* sp. strain, *Neurospora* sp. strain and *Myceliophthora* sp. strain.

29. The method of embodiment 26, wherein the modified strain produces an increased amount of the POI relative to the parental strain when cultivated under the same conditions at 26° C.

30. The method of embodiment 26, wherein the modified strain produces an increased amount of the POI relative to the parental strain when cultivated under the same conditions at 27° C.

31. The method of embodiment 26, wherein the modified strain produces an increased amount of the POI relative to the parental strain when cultivated under the same conditions at 28° C.
32. The method of embodiment 26, wherein the endogenous POI is a lignocellulosic degrading enzyme.
33. The method of embodiment 26, wherein the modified strain further comprises an expression construct encoding a heterologous POI.
34. The method of embodiment 26, wherein the encoded GEF1 protein comprises at least 70% sequence identity to SEQ ID NO: 2.
35. The method of embodiment 26, wherein the encoded GEF1 protein comprises at least 90% sequence identity to the GEF1 domain of SEQ ID NO: 5.
36. The method of embodiment 26, wherein the gene encoding the GEF1 protein comprises at least 70% sequence identity to the GEF1 polynucleotide sequence of SEQ ID NO: 1.
37. The method of embodiment 26, wherein the gene encoding the GEF1 protein comprises at least 70% sequence identity to the open reading frame (ORF) sequence of SEQ ID NO: 3.
38. The method of embodiment 26, wherein the gene encoding the GEF1 protein hybridizes with a GEF1 gene of SEQ ID NO: 1, or a GEF1 ORF of SEQ ID NO: 3, under medium to stringent hybridization conditions.
39. The method of embodiment 26, wherein the genetic modification truncates at least the first 20 amino acid residues of the GEF1 N-terminus, or truncates at least the last 20 amino acid residues of the GEF1 C-terminus.
40. The method of embodiment 26, wherein the genetic modification truncates at least the first 200 amino acid residues of the GEF1 N-terminus, or truncates at least the last 200 amino acid residues of the GEF1 C-terminus.
41. The method of embodiment 26, wherein the genetic modification truncates at least the first 500 amino acid residues of the GEF1 N-terminus, or truncates at least the last 500 amino acid residues of the GEF1 C-terminus.
42. The method of embodiment 26, wherein the genetic modification truncates at least 700 to 750 amino acid residues of the GEF1 C-terminus.
43. The method of embodiment 26, wherein the gene encoding the GEF1 protein is deleted.
44. A method for producing increased amounts of a heterologous protein of interest (POI) in a modified filamentous fungal strain comprising (a) genetically modifying a filamentous fungal strain by disrupting or deleting the native GEF1 gene and by introducing an expression cassette encoding a heterologous POI, and (b) fermenting the modified strain under suitable conditions for the production of the heterologous POI, wherein the modified strain produces an increased amount of the POI relative to the parental strain when cultivated under the same conditions at 25° C.
45. The method of embodiment 44, wherein the filamentous fungus is a Pezizomycotina.
46. The method of embodiment 44, wherein the filamentous fungus is selected from the group consisting of a *Trichoderma* sp. strain, *Aspergillus* sp. strain, *Fusarium* sp. strain, *Penicillium* sp. strain, a *Candida* sp. strain, *Chrysosporium* sp. strain, *Cephalosporium* sp. strain, *Talaromyces* sp. strain, *Neurospora* sp. strain and *Myceliophthora* sp. strain.
47. The method of embodiment 44, wherein the modified strain produces an increased amount of the POI relative to the parental strain when cultivated under the same conditions at 26° C.
48. The method of embodiment 44, wherein the modified strain produces an increased amount of the POI relative to the parental strain when cultivated under the same conditions at 27° C.
49. The method of embodiment 44, wherein the modified strain produces an increased amount of the POI relative to the parental strain when cultivated under the same conditions at 28° C.
50. The method of embodiment 44, wherein the heterologous POI is selected from an enzyme, an antibody or a fragment thereof, a receptor protein and a peptide.
51. The method of embodiment 44, wherein the heterologous POI is an enzyme selected from the group consisting of oxidoreductases, transferases, hydrolases, lyases, isomerases and ligases.
52. The method of embodiment 44, wherein the heterologous POI is an enzyme selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, and hexose oxidases.
53. A protein of interest produced by the method of embodiment 26 or embodiment 44.
54. A method for producing an increased amount of ethanol in a yeast fermentation process comprising (a) genetically modifying a yeast strain by deleting or disrupting the native GEF1 gene, and (b) fermenting the modified strain under suitable conditions for the production of ethanol, wherein the modified strain produces an increased amount of ethanol at the end of fermentation (EOF) relative to the amount of ethanol produced by the parental strain at the EOF when cultivated under the same conditions.
55. A variant yeast strain derived from a parental strain comprising a gene encoding a GEF1 protein homologue, wherein the variant strain comprises a genetic modification which deletes or disrupts the gene encoding the GEF1 protein homologue, wherein the variant strain comprises an increased ethanol productivity phenotype relative to the parental strain when cultivated under the same conditions

EXAMPLES

Certain aspects of the present disclosure may be further understood in light of the following examples, which should not be construed as limiting. Modifications to materials and methods will be apparent to those skilled in the art.

Example 1

Identifying Mutant *Trichoderma* Strains Comprising Enhanced Protein Productivity Phenotypes at Elevated Cultivation Temperatures A *Trichoderma reesei* whole cellulase (T4) strain was serially propagated under selective conditions to isolate mutants capable of high temperature protein production, without adversely affecting specific productivity. A mutant *T. reesei* strain named "T4-E1" was identified and isolated with a similar specific productivity (Qp) at 28° C., relative to the parental *T. reesei* T4 strain at 25° C. For example, the T4 parental strain was sporulated on BIRD agar and $1\times10^7$ spores/mL were collected from the agar plate, suspended in water and treated with 0.15 mg/mL of 1-methyl-3-nitro-1-nitrosoguanidine (Sigma 112, 994-1) for two (2) hours at room temperature until only 1% of the spores remained viable. The spores were inoculated into an evolution media containing 0.5% of either microcrystalline cellulose (EMCOCEL, JRS Pharma, Rosenburg, Germany), carboxymethylcellulose (CMC; Sigma-Aldrich C5678, St. Louis, MO), or acid swollen cellulose (e.g., for preparation see, Wood, 1988) as the sole carbon source. Also, per liter ammonium sulfate (4 g), sodium phosphate monobasic (4.5 g), magnesium sulfate heptahydrate (1 g), calcium chloride dihydrate (1 g) and 2.5 ml of a 400× trace element solution.

More specifically, in a first method, about one (1) million chemically mutated spores were inoculated into a two-hundred fifty (250) ml dented bottom flask containing the evolution medium described above with Avicel® as the sole carbon source. The flask was incubated at 180 rpm, 31° C. for five (5) days. At this time, a 10% volume/volume transfer was made to a second identical flask which was incubated in the same manner. The serial transfer continued for eleven (11) passages (P) as follows: P1=five (5) days, P2=five (5) days, P3=four (4) days, P4=four (4) days, P5=four (4) days, P6=four (4) days, P7=four (4) days, P8=four (4) days, P9=three (3) days, P10=three (3) days and P11=two (2) days. The P11 broth from the P11 shake flasks was centrifuged at 4,000 rpm for ten (10) minutes. The supernatant was discarded and the cells were suspended in water and plated onto BIRD medium.

Individual colony forming units were evaluated for total protein BCA (Product #23228, Thermo Scientific, Rockford, IL) after incubation in a slow-release lactose micro titer plate (srMTP; e.g., see PCT Publication No. WO2014/047520) for four (4) days, 31° C., 200 rpm, and 80% humidity. Thus, mutant strains producing an equivalent amount of total protein at 31° C. relative to the amount of total protein produced by the parental strain at 25° C., were further evaluated for high temperature protein production in fermentors.

In a second method, mutated spores of the *T. reesei* T4 parental strain were encapsulated in water and oil emulsion droplets using methods described in Bachmann et al. (2013). The droplets contained evolution medium with either 0.5% microcrystalline cellulose (EMCOCEL, JRS Pharma, Rosenburg, Germany), carboxymethylcellulose (Sigma-Aldrich C5678, St. Louis, MO), or acid swollen cellulose (Wood, 1988) as the sole carbon source. Also, per liter ammonium sulfate (4 g), sodium phosphate monobasic (4.5 g), magnesium sulfate heptahydrate (1 g), calcium chloride dihydrate (1 g), and 2.5 ml of a 400× trace element solution. The droplets were incubated at 31° C. in a tube for three (3) days at which time the emulsion was disrupted using methods described in Bachmann et al. (2013). The cells were recovered, sporulated on agar plates, re-encapsulated and incubated at 31° C. for three (3) days. This process was repeated 10 times. After the final transfer, the cells were suspended in water and plated onto BIRD medium. Individual colony forming units were evaluated for total BCA protein (Product #23228, Thermo Scientific, Rockford, IL) after incubation in a srMTP lactose plate (PCT Publication No. WO2014/047520) for four (4) days, 31° C., 200 rpm, and 80% humidity. Mutant strains producing an equivalent amount of total protein at 31° C. relative to the amount of total protein produced by the parental strain at 25° C., were further evaluated for high temperature protein production in fermentors. Thus, as generally set forth above and presented below, a mutant *T. reesei* (T4) strain named "T4-E1" was identified as a high temperature mutant capable of optimal protein production at 28° C. compared to (vis-à-vis) the optimal protein production of the parental T4 strain at 25° C.

Example 2

Characteristics of the Mutant *Trichoderma* Strain Comprising A Mutated GEF1 Gene The gene that was mutated in the *Trichoderma* variant (mutant) strain described above in Example 1 resides at scaffold position 3:1532639-1538781 in the wild-type *T. reesei* QM6a v2.0 genome sequence assembly, available at the Joint Genomes Institute (JGI) website (genome.jgi.doe-.gov). For example, the deduced amino acid sequence (PID: 120482; SEQ ID NO: 2) includes a region of sequence homology (e.g., SEQ ID NO: 4) with the Rho/Rac/Cdc42-like guanine nucleotide exchange factor domain (GEF1 domain; Pfam PF00621, also called Dbl-homologous or DH domain). This homologous region is at amino acid residue positions 1,242-1,454 in the deduced amino acid sequence (i.e., PID: 120482; SEQ ID NO: 2). The Rho family GTPases regulate many different cellular processes, wherein such GTPases are activated through release of bound GDP and subsequent binding of GTP, which is catalysed by guanine exchange factors in the GEF1 family. The mutation in the variant T4-E1 strain replaces a glutamate codon (Glu (E); amino acid position 1,245) with a pre-mature stop codon, thereby truncating the protein near the beginning of the GEF1 domain (e.g., see FIG. 3A-3C).

Likewise, the deduced amino acid sequence (PID: 120482; SEQ ID NO: 2) also comprises homology to the BAR or AH/BAR domain (e.g., SEQ ID NO: 5; Pfam PF03114) at residue positions 1,576-1,677 of SEQ ID NO: 2. The AH/BAR domain is found in a range of proteins. In some cases, it has been shown to interact with membranes, dimerize or to bind Arf and Rho family GTPases, including ARF1, a small GTPase involved in vesicle budding at the Golgi complex. The AH/BAR domain (SEQ ID NO: 5) is not observed in the other four (4) *T. reesei* GEF1 domain proteins.

Unlike some other GEF1 domain proteins, no Plekstrin homology domain (PH domain, Pfam PF00169) is found in SEQ ID NO: 2 (PID: 120482). The PH domain can bind phosphatidylinositol in membranes and the beta/gamma subunits of heterotrimeric G proteins or protein kinase C, and thereby is associated with signal transduction pathways. There are four (4) other deduced protein sequences found in the *T. reesei* QM6a genome that contain GEF1 domains, of which two (2) also contain PH domains.

In addition, the deduced amino acid sequence (PID: 120482; SEQ ID NO: 2) includes a C-terminal sequence (e.g., SEQ ID NO: 6) at residue positions 1,918-1,990 of SEQ ID NO: 2 that is highly conserved with some other filamentous fungal GEF1 domain proteins, including *Fusarium fujikuroi, Fusarium graminearum, Thielavia terrestris, Podospora anserina, Penicillium rubens* and *Aspergillus niger*. However, this C-terminal sequence domain (SEQ ID NO: 6) is not in the other four (4) GEF1 domain proteins identified in the *T. reesei* genome.

Example 3

Inactivation of the GEF1 Gene in a *Trichoderma* Strain by Insertion of Pyr2 Gene Inactivation of the GEF1 gene (JGI *T. reesei* v2.0 scaffold 3:1532639-1538781) encoding a GEF1 protein of SEQ ID NO: 2 (PID: 120482) was performed in a *T. reesei* strain using a Cas9-based method. More particularly, purified Cas9 protein and Modified EZ tracrRNA were purchased from Synthego Corporation (Redwood City, CA) and the modified crRNA was synthesized by Synthego with the following sequence at the 5' end (TS3; SEQ ID NO: 7) that is specific to a target site (TS3) within the *T. reesei* GEF1 gene.

```
                              (SEQ ID NO: 7)
TS3: CAUUCAUCCAAGAAUCCGAG
```

The Cas9 target site (TS) in the GEF1 gene, determined by the above RNA sequence (SEQ ID NO: 7) is at nucleotide positions 3,659-3,678 in the coding sequence, which is close to the mutation at nucleotide position 3,733 observed in the T4-E1 mutant strain (Example 2). The tracrRNA and crRNA were annealed to form guide RNA (gRNA) and then combined with Cas9-2NLS to form a ribonucleoprotein complex (Cas9:RNP) according to the manufacturer's directions. Before use, the Cas9:RNP's were mixed with Lipofectamine CRISPR-MAX, purchased from ThermoFisher Scientific, Inc. (Waltham, MA).

A linear DNA fragment containing the *T. reesei* pyr2 gene with native promoter and terminator sequences and flanked by 492 bp of *T. reesei* repeat (SEQ ID NO: 18) was amplified by PCR using primers AL950 (SEQ ID NO: 8) and AL952 (SEQ ID NO: 9) primers. The resulting PCR product was purified using a Qiagen QIAquick PCR purification kit.

```
                              (SEQ ID NO: 8)
AL950: CCTAACTAACGTCTGACATCG

                              (SEQ ID NO: 9)
AL952: CGTACCATTTGACTGATACGATG
```

Protoplasts of the *T. reesei* parental strain were transformed with the pyr2 PCR product plus the Cas9:RNP. Transformants were selected for uridine auxotrophy. Screening transformants for the desired insertion of pyr2 into the GEF1 gene was conducted by PCR using forward and reverse primer pairs RhoF1 (SEQ ID NO: 10) and RhoR1 (SEQ ID NO: 11), which primers amplify across the GEF1 Cas9

```
                              (SEQ ID NO: 10)
RhoF1: GAGCTAGACACGGGCGAAG

                              (SEQ ID NO: 11)
RhoR1: AGGAACCCTTCGTGAGCAAG
```

Insertion of pyr2 increased the size of the PCR product from 755 bp to approximately 2.8 kb. The DNA sequence of the 2.8 kb PCR product from transformant named "ΔRho #22D" was determined by Sanger sequencing using the RhoF1 and RhoR1 primers, verifying insertion of pyr2 at the Cas9 cleavage site and disruption of the GEF1 coding sequence.

As presented in TABLE 1, the fermenter performance of the ΔRho #22D transformant was compared to the parental T4 strain and the mutant named T4-E1 strain described in Example 1. For example, the final specific productivity (Qp) rates of the T4, T4-E1 and T4-ΔRho #22D strains at 28° C. are shown in TABLE 1 as percentages (%) relative to the final Qp rate of the control strain T4 at 25° C.

TABLE 1

| FINAL Qp RATE (g/gDCW/hr) AS PERCENT OF CONTROL (T4 25° C.) | | |
|---|---|---|
| Strain name | Temperature (° C.) | Final Qp Rate % of control (T4 25° C.) |
| T4 | 25 | 100 |
| T4 | 28 | 68 |
| T4-E1 | 28 | 98 |
| T4-ΔRho#22D | 28 | 107 |

Example 4

Inactivation of the GEF1 Gene by Partial Deletion in a *Trichoderma* Strain Comprising a Heterologous Cellulase Expression Construct As described in the instant example, a *Trichoderma* strain named "T4-DXST" was derived/constructed from a parental *T. reesei* T4 strain, wherein the native cellulase genes encoding the CBHI, CBHII, EGI and EGII proteins were inactivated by deletion or disruption (i.e., using routine molecular biology techniques known by one of skill in the art), and transformed with copies of the gene encoding *Staphylotrichum coccosporum* endoglucanase 1 (STCE1) placed under the control of the high efficiency cbhI promoter.

Methods for transformation of *T. reesei* with exogenously added plasmid DNA have been published (Penttila et al., 1986; Gruber et al., 1990; Smith et al., 1991). Stable transformants arise by integration of plasmid DNA into the chromosomes of the host. Integration can be at sites in the genome that have homology with a region of the plasmid DNA or can be at non-homologous sites.

Inactivation of the gene encoding GEF1 in a parental *T. reesei* strain comprising copies of the introduced STCE1 cellulase construct (e.g., see U.S. Pat. No. 7,595,182) was performed using a Cas9-based method. More particularly, purified Cas9-2NLS protein and Modified EZ tracrRNA were purchased from Synthego Corporation (Redwood City, CA). Modified crRNAs were synthesized by Synthego with the following RNA sequences at the 5' end that are specific to target sites 3 and 4 (TS3/TS4) within the *T. reesei* GEF1 gene.

```
                                    (SEQ ID NO: 7)
TS3: CAUUCAUCCAAGAAUCCGAG

                                   (SEQ ID NO: 12)
TS4: AUUGUGGAGGAAAUCUACAA
```

The Cas9 target sites (TS3/TS4) in the GEF1 gene determined by the above RNA sequences are at nucleotide positions 3,659-3,678 and at nucleotide positions 3,775-3794 in the coding sequence, which is close to the mutation at nucleotide position 3,733 observed in the T4-E1 mutant strain. The tracrRNA and crRNA were annealed to form guide RNA (gRNA) and then combined with Cas9-2NLS to form a ribonucleoprotein complex (Cas9:RNP), according to the manufacturer's directions. Before use, the Cas9:RNP's were mixed with Lipofectamine CRISPR-MAX purchased from ThermoFisher Scientific, Inc. (Waltham, MA).

A linear DNA fragment containing a bacterial hygromycin phosphotransferase gene (SEQ ID NO: 13) operably linked to the *Neurospora crassa* cpcl promoter (SEQ ID NO: 14) and *Aspergillus nidulans* trpC terminator (SEQ ID NO: 15) was amplified by PCR using primers HygF1 (SEQ ID NO: 16) and HygR1 (SEQ ID NO: 17).

```
                                   (SEQ ID NO: 16)
HygF1: TGGCTTTCCGTCTCCATTG

                                   (SEQ ID NO: 17)
HygR1: AGTGTACCTGTGCATTCTGGG
```

Protoplasts of the *T. reesei* parental strain were transformed with the linear DNA fragment and a mixture of both Cas9:RNP's (with both crRNAs). Transformants were selected for hygromycin resistance on appropriate agar medium. However, only smaller and slower growing transformed colonies were picked from the selective agar plates and were transferred to agar plates with non-selective medium. After growth on the non-selective medium, transformants were picked and spotted onto medium with hygromycin. Transformants that did not grow in the presence of hygromycin were chosen for further study. It was presumed that these transformants had exhibited hygromycin resistance transiently, and had subsequently lost the hygromycin-resistance DNA marker fragment without integration into the *T. reesei* genome. PCR with the RhoF1 (SEQ ID NO: 10) and RhoR1 (SEQ ID NO: 11) primers was used to screen the hygromycin-sensitive transformants.

Transformants were identified that gave a PCR product of approximately 630 bp, as expected if a deletion between Cas9 target sites TS3 and TS4 had occurred. The size of this PCR product in wild-type cells is 756 bp. The PCR products were sequenced from each end using primers RhoF1 (SEQ ID NO: 10) and RhoR1 (SEQ ID NO: 11). Transformant #89 (t-AWC88) had a 125 bp deletion (i.e., nucleotide positions 3,668-3,791 in the coding sequence) between TS3 and TS4 with no insertion. The *Trichoderma* transformant #89 (t-AWC88) was subsequently fermented and compared (vis-à-vis) to the parental strain (t-AVT84) for STCE/DXST protein production at 25° C. and 28° C. as presented in TABLE 2.

TABLE 2

FINAL PROTEIN YIELD DURING PRODUCTION PHASE AS PERCENT OF CONTROL STRAIN t-AVT84 AT 25° C.

| Strain Name | Temperature (° C.) | Final Yield (g/g) % of Control (t-AVT84 25° C.) |
|---|---|---|
| t-AVT84 | 25 | 100 |
| t-AVT84 | 28 | 58 |
| t-AWC88 | 25 | 111 |
| t-AWC88 | 26 | 106 |
| t-AWC88 | 27 | 106 |
| t-AWC88 | 28 | 78 |
| t-AWC88 | 30 | 55 |

More particularly, as shown above in TABLE 2, the T4-DXST daughter strain (t-AWC88) has at least a 2-3° C. higher protein production temperature optimum relative to the parental strain (t-AVT84).

REFERENCES

PCT Application Serial No. PCT/US2019/27590

PCT Publication No. WO2011/153449

PCT Publication No. WO2012/145584

PCT Publication No. WO2012/145595

PCT Publication No. WO2016/100272

PCT Publication No. WO2016/100562

PCT Publication No. WO2016/100568

U.S. Pat. No. 6,022,725

U.S. Pat. No. 6,255,115.

U.S. Pat. No. 6,268,328

U.S. Pat. No. 7,595,182

U.S. Provisional Application Ser. No. 62/711,846, filed Jul. 30, 2018.

Altschul et al., *J. Mol. Biol.* 215:403-10, 1990.

Altschul et al., *Meth. Enzymol.* 266:460-80, 1996.

Ausubel et al., "Current Protocols in Molecular Biology", Green Publishing Associates/Wiley Interscience, New York, 1994.

Bachmann et al., "Availability of public goods shapes the evolution of competing metabolic strategies", *PNAS,* 110 (35): 14302-14307, 2013.

Boel et al., *EMBO J* 3:1581-1585, 1984.

Botstein and Shortle, *Science* 229: 4719, 1985.

Campbell et al., *Curr. Genet.,* 16: 53-56, 1989.

Cao et al., *Science,* 9: 991-1001, 2000.

Devereux et al., *Nucleic Acids Res.* 12:387-395, 1984.

Gruber et al., 1990

Hakkinen et al., "Screening of candidate regulators for cellulase and hemicellulase production in *Trichoderma reesei* and identification of a factor essential for cellulase production", *Biotechnol Biofuels* 7, 14, 2014.

Harkki et al., *BioTechnol.,* 7: 596-603, 1989.

Harkki et al., *Enzyme Microb. Technol.,* 13: 227-233, 1991.

Henikoff and Henikoff, *Proc. Natl. Acad. Sci. USA* 89:10915, 1989.

Higgins and Sharp, *CABIOS* 5:151-53, 1989.

Higuchi et al., *Nucleic Acids Research* 16: 7351, 1988.

Ho et al., *Gene* 77: 61, 1989.

Horton et al., *Gene* 77: 61, 1989.

Iglesias and Trautner, *Molecular General Genetics* 189: 73-76, 1983.

Joint Genomes Institute (JGI) website (www.genome.jgi.doe.gov).

Karlin et al., *Proc. Natl. Acad. Sci. USA* 90:5873-87, 1993.

Lo et al., *Proceedings of the National Academy of Sciences USA* 81: 2285, 1985.

Mullaney et al., *MGG* 199:37-45, 1985.

Needleman and Wunsch, *J. Mol. Biol.,* 48:443, 1970.

Nunberg et al., *Mol. Cell Biol.* 4:2306, 1984.

Parish and Stoker, *FEMS Microbiology Letters* 154: 151-157, 1997. Pearson and Lipman, 1988

Penttila et al., "A versatile transformation system for the cellulolytic filamentous fungus *Trichoderma reesei", Gene* 61, 155-164, 1987.

Perego, 1993, In A. L. Sonneshein, J. A. Hoch, and R. Losick, editors, *Bacillus subtilis and Other Gram-Positive Bacteria*, Chapter 42*, American Society of Microbiology*, Washington, D.C.

Sambrook et al., "*Molecular Cloning, A Laboratory Manual*", 4th Edition, *Cold Spring Harbor Laboratory Press*, Cold Spring, New York, 2012.

Sarkar and Sommer, *BioTechniques* 8: 404, 1990.

Shimada, *Meth. Mol. Biol.* 57: 157; 1996.

Smith and Waterman, *Adv. Appl. Math.* 2:482, 1981.

Wood, "Preparation of crystalline, amorphous, and dyed cellulase substrates", *Methods in Enzymology*, Vol. 160, pages 19-25, 1988.

Yelton et al., *PNAS USA* 81:1470-1474, 1984.

Youngman et al., 1983

The invention claimed is:

1. A variant filamentous fungal cell derived from a parental cell comprising a gene encoding a protein having at least 80% identity to SEQ ID NO: 2, wherein the variant cell comprises a genetic modification which disrupts or deletes the gene encoding the protein having at least 80% identity to SEQ ID NO: 2, wherein the variant cell comprises an enhanced protein productivity phenotype relative to the parental cell when fermented under the same conditions.

2. The variant cell of claim 1, wherein the enhanced protein productivity phenotype is selected from the group consisting of increased protein productivity, increased total protein productivity, increased volumetric productivity, increased carbon conversion efficiency and increased specific productivity.

3. The variant cell of claim 1, comprising an increased protein productivity phenotype relative to the parental cell when the variant and parental cells are fermented under the same conditions at 25° C.

4. The variant cell of claim 1, comprising a gene encoding an endogenous protein of interest (POI) and/or comprising an expression cassette encoding a heterologous POI.

5. The variant cell of claim 4, wherein the endogenous POI is a lignocellulosic degrading enzyme.

6. The variant cell of claim 5, wherein the lignocellulosic degrading enzyme is selected from the group consisting of a cellobiohydrolase, a xylanase, an endoglucanase and a β-glucosidase.

7. The variant cell of claim 4, wherein the expression cassette encodes a heterologous POI selected from an enzyme, an antibody, a receptor and a peptide.

8. The variant cell of claim 7, wherein the enzyme is selected from the group consisting of oxidoreductases, transferases, hydrolases, lyases, isomerases and ligases.

9. A method for producing an increased amount of an endogenous protein of interest (POI) in a modified filamentous fungal cell comprising:

(a) genetically modifying a parental filamentous fungal cell by disrupting or deleting a gene encoding a protein having at least 80% identity to SEQ ID NO: 2, and (b) fermenting the modified cell under suitable conditions for the production of the POI, wherein the modified cell produces an increased amount of the POI relative to the parental strain when fermented under the same conditions at 25° C.

10. The method of claim 9, wherein the endogenous POI is a lignocellulosic degrading enzyme.

11. The method of claim 10, wherein the lignocellulosic degrading enzyme is selected from the group consisting of a cellobiohydrolase, a xylanase, an endoglucanase and a β-glucosidase.

12. The method of claim 9, wherein the modified strain further comprises an expression construct encoding a heterologous POI.

13. A method for producing an increased amount of a heterologous protein of interest (POI) in a modified filamentous fungal cell comprising:

(a) genetically modifying a filamentous fungal cell expressing a heterologous POI, wherein the cell is modified by disrupting or deleting a gene encoding a protein having at least 80% identity to SEQ ID NO: 2, and (b) fermenting the modified cell under suitable conditions for the production of the heterologous POI, wherein the modified cell produces an increased amount of the POI relative to the parental strain when fermented under the same conditions at 25° C.

14. The method of claim 13, wherein the heterologous POI is selected from an enzyme, an antibody or a fragment thereof, a receptor protein and a peptide.

15. The method of claim 13, wherein the heterologous POI is an enzyme selected from the group consisting of oxidoreductases, transferases, hydrolases, lyases, isomerases and ligases.

* * * * *